(12) United States Patent
Paul et al.

(10) Patent No.: US 12,702,358 B2
(45) Date of Patent: Aug. 11, 2026

(54) DYNAMIC INCREMENTAL ANALOG-TO-DIGITAL CONVERSION INTERFACES FOR IN-EAR ELECTROPHYSIOLOGY

(71) Applicant: The Regents of the University of California, Oakland, CA (US)

(72) Inventors: Akshay Paul, San Diego, CA (US); Preston Fowler, San Diego, CA (US); Yuchen Xu, San Diego, CA (US); Jun Wang, San Diego, CA (US); Gert Cauwenberghs, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 237 days.

(21) Appl. No.: 18/570,534

(22) PCT Filed: Jun. 15, 2022

(86) PCT No.: PCT/US2022/033673
§ 371 (c)(1),
(2) Date: Dec. 14, 2023

(87) PCT Pub. No.: WO2022/266252
PCT Pub. Date: Dec. 22, 2022

(65) Prior Publication Data

US 2024/0268757 A1 Aug. 15, 2024

Related U.S. Application Data

(60) Provisional application No. 63/210,916, filed on Jun. 15, 2021.

(51) Int. Cl.
*A61B 5/00* (2006.01)
*A61B 5/0205* (2006.01)
(Continued)

(52) U.S. Cl.
CPC .......... *A61B 5/6817* (2013.01); *A61B 5/0002* (2013.01); *A61B 5/02055* (2013.01);
(Continued)

(58) Field of Classification Search
CPC . A61B 5/6817; A61B 5/0002; A61B 5/02055; A61B 5/31; A61B 5/315;
(Continued)

(56) References Cited

U.S. PATENT DOCUMENTS 11,471,103 B2 * 10/2022 LeBoeuf .............. A61B 5/0084
2012/0194372 A1 * 8/2012 Venkatraman .......... H03M 3/04
341/143

(Continued)

FOREIGN PATENT DOCUMENTS

WO WO-2019162518 A1 * 8/2019 ............. H04R 1/028
WO WO-2021061218 A1 4/2021

OTHER PUBLICATIONS

Abbott, J et al., "The Design of a CMOS Nanoelectrode Array with 4096 Current-Clamp/Voltage-Clamp Amplifiers for Intracellular Recording/Stimulation of Mammalian Neurons," IEEE Journal of Solid-State Circuits, Sep. 2020, 55(9): 2567-2582.

(Continued)

*Primary Examiner* — Eliza A Lam
(74) *Attorney, Agent, or Firm* — FisherBroyles, LLP

(57) ABSTRACT

In some implementations, the current subject matter relates a system including an in-ear housing configured to fit in an ear of a wearer; a flexible printed circuit mounted within the in-ear housing; and an analog to digital converter comprising a neural interface system-on-chip having dynamic incremental successive-approximation register acquisition to process signals detected by at least one electrode disposed on or near a surface of the in-ear housing. Related systems, methods, and articles of manufacture are also disclosed.

20 Claims, 23 Drawing Sheets

(51) Int. Cl.
*A61B 5/291* (2021.01)
*A61B 5/297* (2021.01)
*A61B 5/31* (2021.01)
*A61B 5/315* (2021.01)

(52) U.S. Cl.
CPC ................ *A61B 5/31* (2021.01); *A61B 5/315* (2021.01); *A61B 5/291* (2021.01); *A61B 5/297* (2021.01); *A61B 2562/0209* (2013.01); *A61B 2562/04* (2013.01); *A61B 2562/164* (2013.01); *A61B 2562/166* (2013.01)

(58) Field of Classification Search
CPC . A61B 5/291; A61B 5/297; A61B 2562/0209; A61B 2562/04; A61B 2562/164; A61B 2562/166; A61B 2560/0214; A61B 5/0006; A61B 5/0008; A61B 5/0022; A61B 5/01; A61B 5/0245; A61B 2562/0219; A61B 2562/0271; A61B 5/6803; A61B 5/256; A61B 5/28; A61B 5/7225
See application file for complete search history.

(56) References Cited

U.S. PATENT DOCUMENTS

| | | | | |
|---|---|---|---|---|
| 2017/0258329 | A1 | 9/2017 | Marsh | |
| 2018/0103858 | A1* | 4/2018 | Marcus | A61B 5/6803 |
| 2018/0206788 | A1 | 7/2018 | Andersen | |
| 2019/0126047 | A1 | 5/2019 | Kassiri Bidhendi et al. | |
| 2019/0282817 | A1 | 9/2019 | Muller et al. | |
| 2021/0099815 | A1* | 4/2021 | Silberzahn | A61B 5/6817 |
| 2024/0007777 | A1* | 1/2024 | Sacha | H04R 25/609 |

OTHER PUBLICATIONS

Aziz, J. et al., “256-channel neural recording microsystem with on-chip 3D electrodes.” In 2007 IEEE International Solid-State Circuits Conference. Digest of Technical Papers (pp. 160-161; 594), Feb. 2007.

De Dorigo, D. et al. “Fully Immersible Subcortical Neural Probes with Modular Architecture and a Delta-Sigma ADC Integrated Under Each Electrode for Parallel Readout of 144 Recording Sites.” IEEE Journal of Solid-State Circuits 53.11 (2018): 3111-3125.

Joshi, S. et al., “2pJ/MAC 14b 8×8 Linear Transform Mixed-Signal Spatial Filter in 65nm CMOS with 84db Interference Suppression.” In 2017 IEEE International Solid-State Circuits Conference (ISSCC) (pp. 364-365), Feb. 2017.

Khurana, H.S. et al., “Recode Then LSB-first Sar Adc for Reducing Energy and Bit-cycles.” IEEE International Symposium on Circuits and Systems (ISCAS’2018), 2018.

Kim, C. et al., “Sub-? Vrms-Noise Sub-?W/Channel ADC-Direct Neural Recording With 200-mV/ms Transient Recovery Through Predictive Digital Autoranging.” IEEE Journal of Solid- State Circuits, vol. 53 (11), pp. 3101-3110, 2018.

Kim, C. et al., “A 92dB Dynamic Range Sub-?V RMS-Noise 0.8 ?W/ch Neural-Recording ADC Array with Predictive Digital Autoranging.” In 2018 IEEE International Solid-State Circuits Conference—(ISSCC) (pp. 470-472), Feb. 2018.

Lopez, C.M. et al., “A 16384-Electrode 1024-Channel Multimodal Cmos Mea for High- Throughput Intracellular Action Potential Measurements and Impedance Spectroscopy in Drug-Screening Applications.” In 2018 IEEE International Solid-State Circuits Conference—Feb. 2018.

Manickam, A. et al., “A CMOS Biosensor Array with 1024 3-Electrode Voltammetry Pixels and 93dB Dynamic Range.” In 2019 IEEE International Solid-State Circuits Conference—(ISSCC) (pp. 192-194). IEEE. (ISSCC) (pp. 464-466), Feb. 2019.

Musk E. et al. “An Integrated Brain-Machine Interface Platform with Thousands of Channels.” J Med Internet Res 2019;21(10): e16194.

Sutor, B. et al. “Voltage-clamp-controlled current-clamp recordings from neurons: an electrophysiological technique enabling the detection of fast potential changes ar reset holding potentials,” Pflugers Archive, Eur J Physiology, (2003) 446:133-141.

Wang et al., “1024-Electrode Hybrid Voltage/Current-Clamp Neural Interface system-on-Chip with Dynamic Incremental-SAR Acquisition,” 2020 IEEE Symposium on VLSI Circuits, Aug. 10, 2020.

Yaul, F.M. et al., “A 10 bit SAR ADC With Data-Dependent Energy Reduction Using LSB-First Successive Approximation.” IEEE Journal of Solid-State Circuits, vol. 49 (12), pp. 2825-2834, Dec. 2014.

Yaul, F.M. et al., “A 10b 0.6 nW SAR ASX with Data-Dependent Energy Savings Using LSB-First Successive Approximation.” In 2014 IEEE International Solid-State Circuits Conference Digest of Technical Papers (ISSCC) (pp. 198-199), Feb. 2014.

Zhang, Z. et al., “A Dynamic Tracking Algorithm Based Sap Adv in Bio-Related Applications,” IEEE Access 6 (2018): 62166-62173.

* cited by examiner 230
102
214
216
232
212
voltage clamp mode
Electrode
Current Clamp
Voltage Clamp
Current Recording
Voltage Recording
Gain
Bandwidth
RST
X1
to ADC 406
408
SAR: 800mV 421
SAR: 8mV 423
/SAR: 800mV, 10Hz (Slow Artifact) 425
/SAR: 800mV, 1000Hz (Fast Artifact) 427
/SAR: 8mV, 10Hz (LFP) 429
/SAR: 8mV, 1000Hz (Spike) 431
421
423
425
427
429
431
Energy/Level (fJ)
Cycles
SAR @ 10.9 ENOB
/SAR @ 11.2 ENOB
Energy/Level (fJ)
Amplitude*Frequency (mV/s)

Figure 13A:
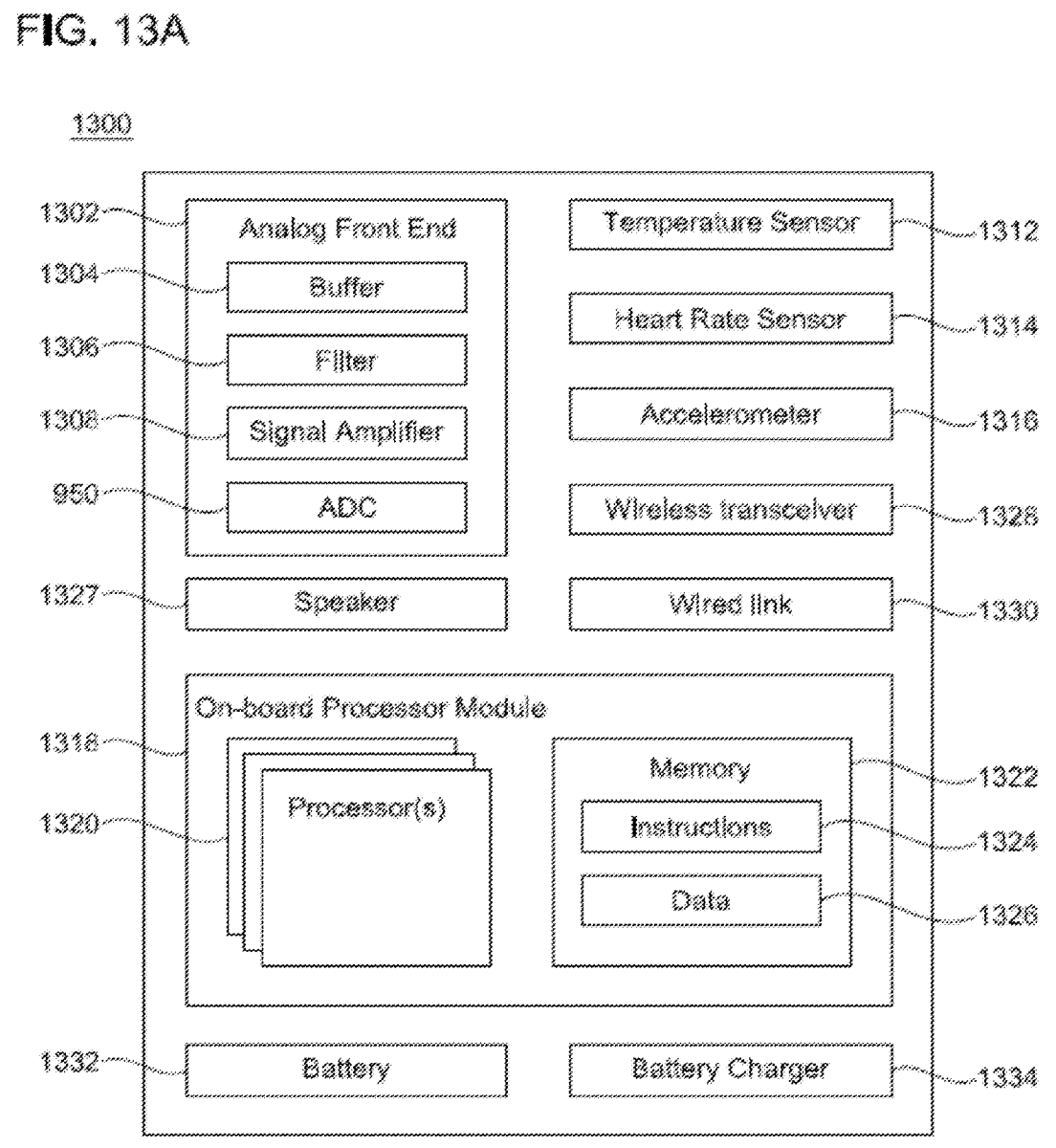

Temperature Sensor 1312
Heart Rate Sensor 1314
Accelerometer 1316
Wireless transceiver 1328
Wired link 1330
Memory 1322
Instructions 1324
Data 1326
Battery Charger 1334
Analog Front End 1302
Buffer 1304
Filter 1306
Signal Amplifier 1308
ADC 950
Speaker 1327
On-board Processor Module 1318
Processor(s) 1320
Battery 1332

Figure 13B:
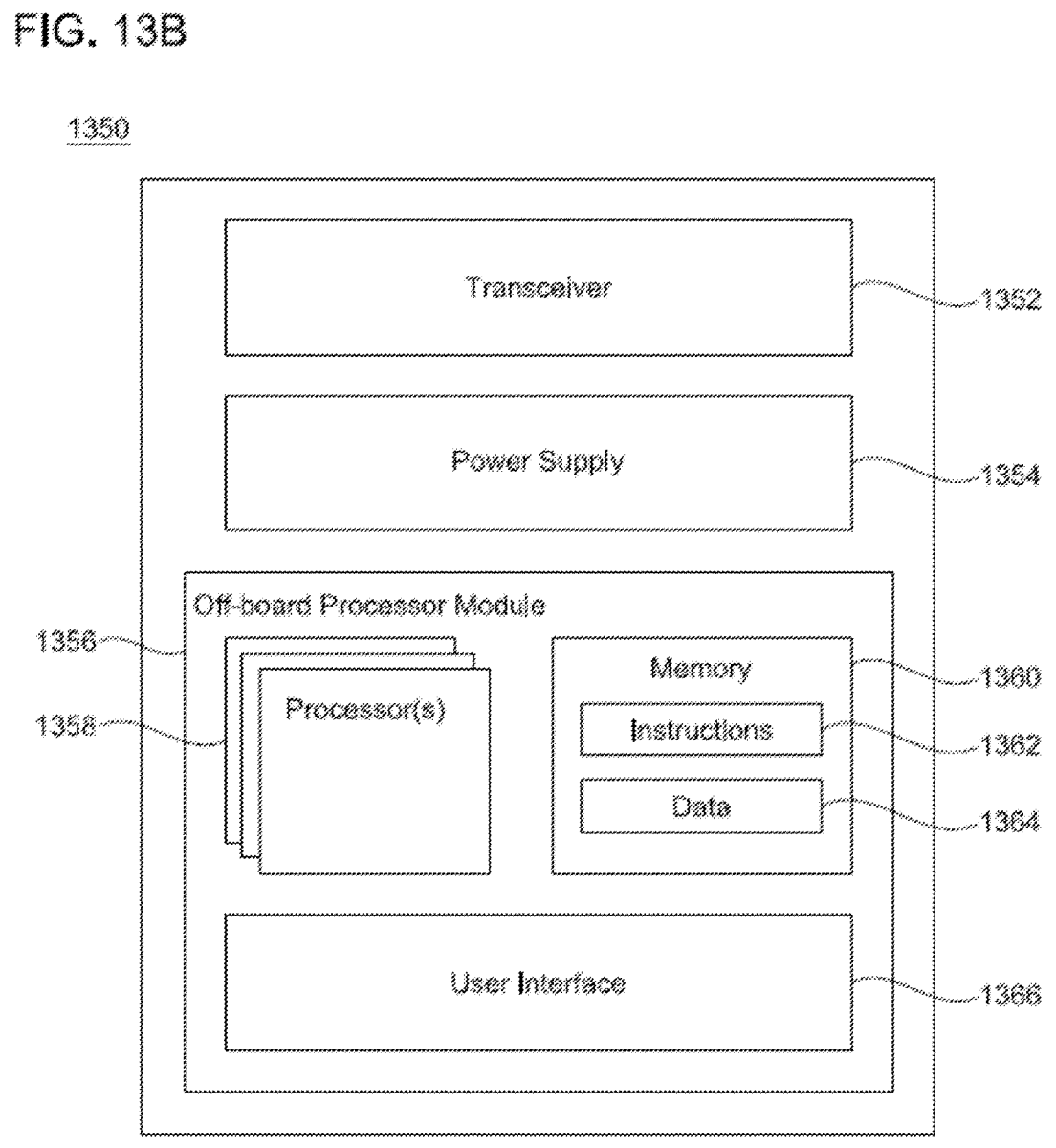

Transceiver 1352

Power Supply 1354

Off-board Processor Module 1356

Processor(s) 1358

Memory 1360

Instructions 1362

Data 1364

User Interface 1366

RSL
CONV
fconv
Done_Check
Strobe
1702

RSL
CONV
fconv
Done_Check
Strobe
CDS_Master
1704

Strobe
ADDR_RST
ADDR_INC
(ADDR)
SPI_READ
SPI_CLK
SPI_OUT
Channel 1
Channel 2
Ch. 3
Ch. 32
Ch. 1
Ch1 Data
Ch2 Data
1706

DYNAMIC INCREMENTAL ANALOG-TO-DIGITAL CONVERSION INTERFACES FOR IN-EAR ELECTROPHYSIOLOGY

CROSS-REFERENCE TO RELATED APPLICATIONS

This application is a national stage entry of Patent Cooperation Treaty Application No. PCT/US2022/033673 filed Jun. 15, 2022, entitled "DYNAMIC INCREMENTAL ANALOG-TO-DIGITAL CONVERSION INTERFACES FOR IN-EAR ELECTROPHYSIOLOGY," which claims priority to U.S. Provisional Application No. 63/210,916 filed Jun. 15, 2021, entitled "DYNAMIC INCREMENTAL-SAR ANALOG-TO-DIGITAL CONVERSION". The disclosures of which are incorporated herein by reference in their entirety.

The present application relates to International Patent Application No. PCT/US21/37478, filed Jun. 15, 2021, and entitled "Dynamic Incremental-SAR Analog-To-Digital Conversion", which claims priority to U.S. Provisional Patent Appl. No. 63/039,452 to Wang et al., filed Jun. 15, 2020, and entitled "Dynamic Incremental-SAR Analog-To-Digital Conversion", and incorporates their disclosures herein by reference in their entireties.

TECHNICAL FIELD

The subject matter disclosed herein relates to a method and apparatus for efficient analog-to-digital conversion, and in particular, to dynamic incremental analog-to-digital conversion interfaces for in-ear electrophysiology.

BACKGROUND

Many types of signals from sensors or sensor arrays have wide dynamic range, but most of the time change relatively little between consecutive samples. Examples of such signals are various physiological indicators of health and wellness in wearable or implantable biosensors, such as blood pressure, photoplesmography (PPG), electrocardiogramhy (ECG), and electrochemical concentrations in cardiovascular and metabolic health sensing, and the electroencephalogram (EEG), electrocorticogram (ECOG) and spike neural recordings in brain activity monitoring.

SUMMARY

In some implementations, the current subject matter relates a system including an in-ear housing configured to fit in an ear of a wearer; a flexible printed circuit mounted within the in-ear housing; and an analog to digital converter comprising a neural interface system-on-chip having dynamic incremental successive-approximation register acquisition to process signals detected by at least one electrode disposed on or near a surface of the in-ear housing.

In some variations, one or more of the features disclosed herein including the following features can optionally be included in any feasible combination. The in-ear housing comprises a malleable material that compresses for insertion into an ear canal of the wearer to enable contact at one or more points within the ear canal. The flexible printed circuit board includes one or more conductive wires, wherein the conductive wires each terminate at a corresponding electrode that senses signals and carry the signals to a common interface, wherein the common interface is coupled to the analog to digital converter. The analog to digital converter is remote from the in-ear housing. The analog to digital converter is contained within the in-ear housing. The at least one electrode comprises a plurality of electrodes arranged as a plurality of conductive rings positioned on the exterior surface of the in-ear housing. The analog to digital converter is comprised in a processing system including an analog front end, wherein the analog front end couples to a buffer, a filter, and a signal amplifier to process and convert the signals. The processing system further includes one or more of the following: a temperature sensor to sense temperature of a wearer of the in-ear housing, a heart rate sensor to sense a heart rate of the wearer, an accelerometer, a wireless transceiver, a wired link, a speaker, at least one processor, at least one memory, and a source of power. The processing system couples via a wireless link to a remote processing system, wherein the remote processing system includes one or more of the following: a wireless transceiver to communicate with a corresponding wireless transceiver at the processing system, at least one processor, at least one memory, a source of power, and a user interface subsystem from which information regarding data processed by the processing system and/or remote processing system may be obtained for further processing or viewing. The signals comprise one or more of the following: an electroencephalography (EEG) of a wearer, an electrooculography (EOG) of a wearer, a temperature of the wearer, a heart rate of the wearer, sound, and acceleration.

In some implementations, the current subject matter relates a system including A method comprising: detecting, by at least one electrode, signals, wherein the at least one electrode is disposed in on or near a surface of an in-ear housing, wherein the in-ear housing configured to fit in an ear of a wearer, wherein the in-ear housing is comprised in a system further including a flexible printed circuit mounted within the in-ear housing and an analog to digital converter comprising a neural interface system-on-chip having dynamic incremental successive-approximation register acquisition; and converting, by the analog to digital converter comprising the neural interface system-on-chip signals, the detected signals to a digital form.

In some variations, one or more of the features disclosed herein including the following features can optionally be included in any feasible combination. The in-ear housing comprises a malleable material that compresses for insertion into an ear canal of the wearer to enable contact at one or more points within the ear canal. The flexible printed circuit board includes one or more conductive wires, wherein the conductive wires each terminate at a corresponding electrode that senses signals and carry the signals to a common interface, wherein the common interface is coupled to the analog to digital converter. The analog to digital converter is remote from the in-ear housing. The analog to digital converter is contained within the in-ear housing. The at least one electrode comprises a plurality of electrodes arranged as a plurality of conductive rings positioned on the exterior surface of the in-ear housing. The analog to digital converter is comprised in a processing system including an analog front end, wherein the analog front end couples to a buffer, a filter, and a signal amplifier to process and convert the signals. The processing system further includes one or more of the following: a temperature sensor to sense temperature of a wearer of the in-ear housing, a heart rate sensor to sense a heart rate of the wearer, an accelerometer, a wireless transceiver, a wired link, a speaker, at least one processor, at least one memory, and a source of power. The processing system couples via a wireless link to a remote processing system, wherein the remote processing system includes one or more of the following: a wireless transceiver to communicate with a corresponding wireless transceiver at the processing system, at least one processor, at least one memory, a source of power, and a user interface subsystem from which information regarding data processed by the processing system and/or remote processing system may be obtained for further processing or viewing. The signals comprise one or more of the following: an electroencephalography (EEG) of a wearer, an electrooculography (EOG) of a wearer, a temperature of the wearer, a heart rate of the wearer, sound, and acceleration.

Implementations of the current subject matter can include methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a non-transitory computer-readable or machine-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including, for example, to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to the virtualization of configuration data, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 13A illustrates an in-ear sensor assembly, according to some implementations of the current subject matter;

FIG. 13B illustrates an external processing system, according to some implementations of the current subject matter;

DETAILED DESCRIPTION

One or more implementations of the current subject matter relate to methods, systems, articles of manufacture, and the like that may, among other possible advantages, provide for systems, devices, and/or methods for providing a neural interface system-on-chip with dynamic incremental successive-approximation register acquisition.

Figure 3A:
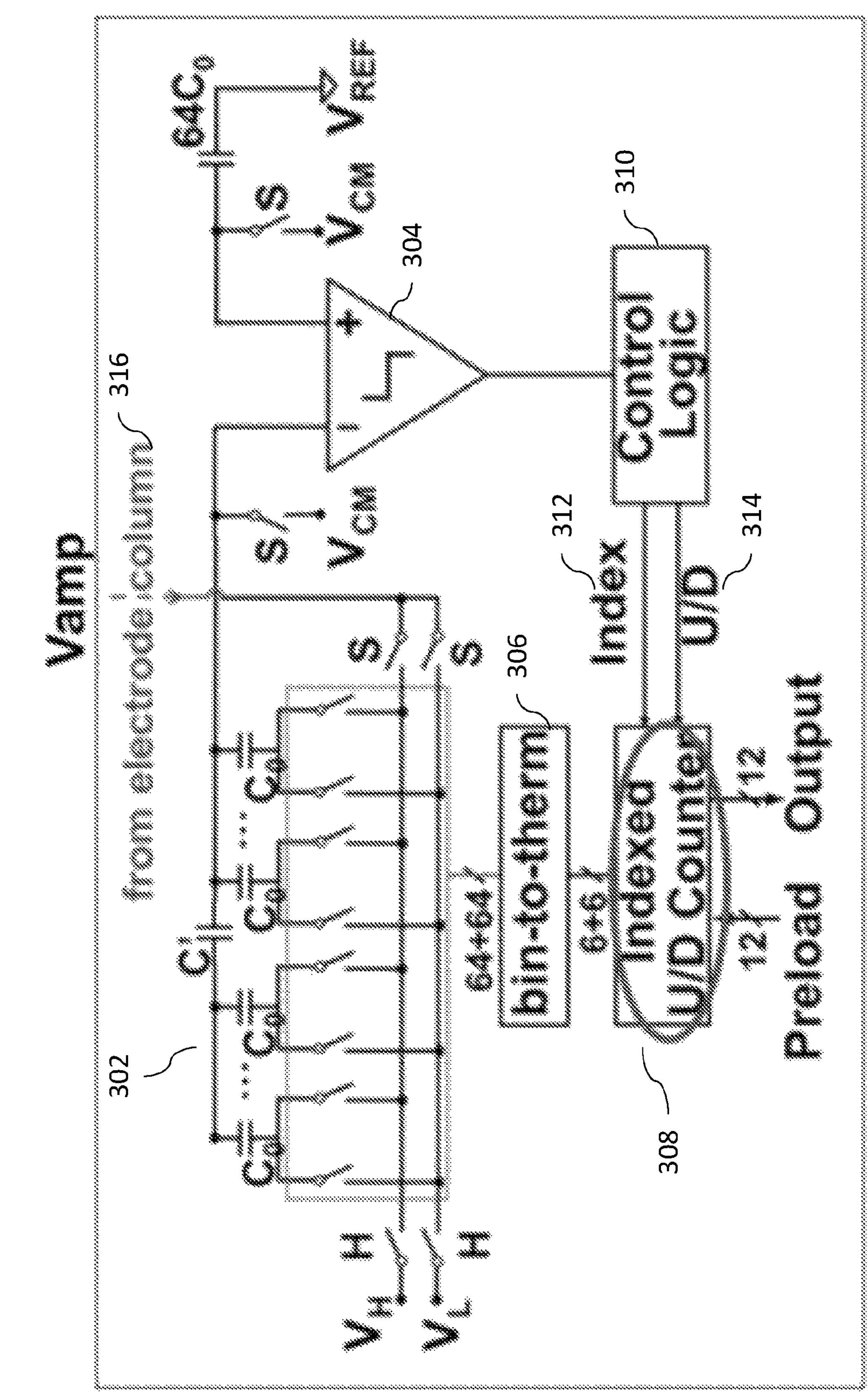
FIG. 3*a* illustrates an exemplary on-chip analog to digital converter(s) shown in FIG. 1, according to some implementations of the current subject matter.
Figure 3B:
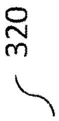
FIG. 3*b* illustrates an exemplary plot illustrating a search path for a SAR operating mode.
Figure 3B:
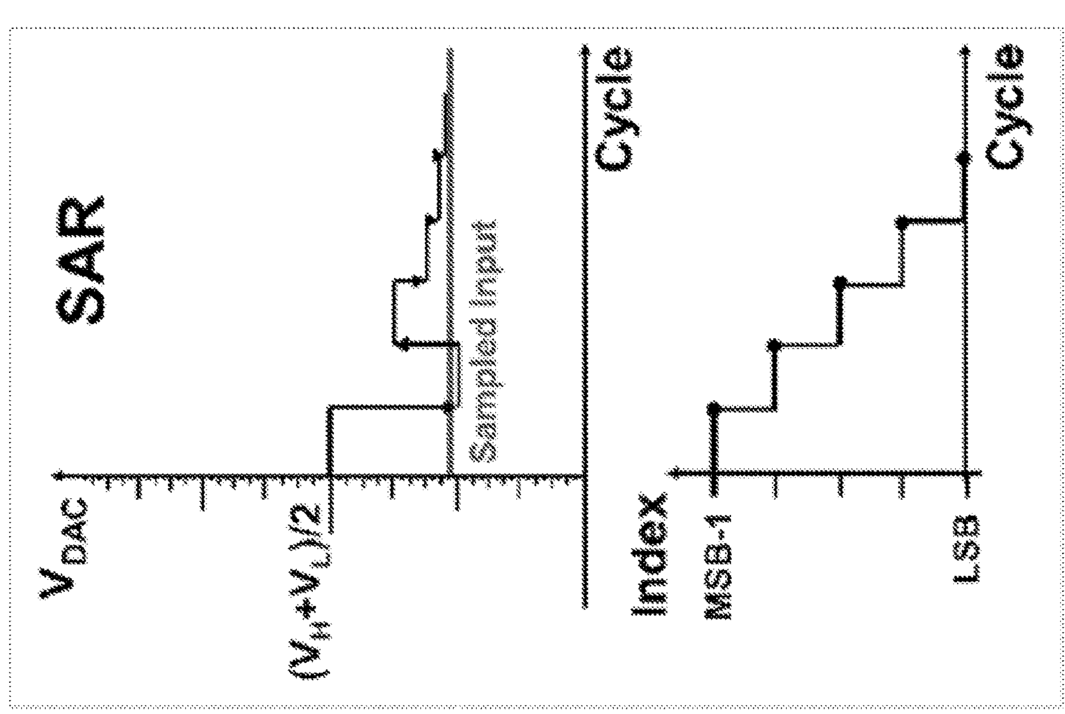

A successive-approximation register (SAR) analog-to-digital converter (ADC) is widely used as one of the most energy efficient architectures available for digitization of analog signals at medium (8-bit to 16-bit) resolution. A conventional SAR ADC performs a binary search (e.g., as shown in FIG. 3*b*, top portion) through level comparisons for the nearest quantized level in a series of successively twice smaller steps, cycling from most-significant bit (MSB) through least-significant bit (LSB) by zooming in two-fold starting from the mid-range level (e.g., as shown in FIG. 3*b*, bottom portion). As such, SAR binary search is most efficient for full-Nyquist memory-less, uniformly distributed signals, but is a poor match for these sensor signals that are mostly very small in amplitude with substantial low-frequency content and infrequent large fast transients. One of the existing systems proposes LSB-first SAR to increase energy efficiency. However, despite several advantages, one of the drawbacks of the LSB-first SAR technique is that the number of cycles (i.e., successive approximation steps) per conversion depends on the previous signal amplitude, and can be very long even for subtle (LSB-level) changes. For instance, it may require 12 cycles to complete conversion in case the previous output is 100000000000 and the current sample input is 011111111111. Another disadvantage of the LSB-first SAR is that it might not be able to accurately follow rapid changes in the input, such as, sharp action potentials, because of digital-to-analog conversion (DAC) charge loss due to the DAC voltage exceeding supply rails. Another existing system includes an improved LSB-first SAR ADC strategy to overcome the latter problem. However, this system still suffers from potentially strong data dependence in the number of conversion cycles to reach nominal precision. Further, similar to conventional SAR, both of the existing LSB-first SAR ADCs are prone to errors in the analog comparison process, which can result in errors in the digital readout as large as half of the signal range.

In some implementations, to overcome the above challenges of existing systems, the subject matter relates to a dynamic incremental-SAR (iSAR) ADC which provides for fast and reliable conversion for slowly varying signals. The iSAR may incrementally advance from the previous ADC result, proceeding in a number of successive approximation steps (e.g., cycles) that may be much lower than the number of ADC bits. For each cycle, the iSAR may dynamically adjust the SAR on a variable radix-2 base to expand and/or contract the search region depending on whether the signal value is detected within the region. In contrast to conventional SAR systems (including the LSB-first SAR ADC), the number of iSAR conversion cycles may be independent of signal amplitude, and may decrease with decreasing magnitude of change (and/or slope) in signal amplitude. Further, iSAR may recover from errors in the analog comparison at the expense of additional conversion cycles, thereby avoiding catastrophic readout errors that are present in conventional SAR systems (including LSB-first SAR ADC). For typical biosignals, iSAR may reach ADC resolution-limited precision in just 3 successive approximation steps between consecutive samples at the Nyquist range, thereby leading to substantial energy savings in signal acquisition.

To cover wider signal range without compromising energy efficiency of existing signal dependent LSB-first SAR ADC, the current subject matter relates to a dynamic incremental SAR (iSAR) with adaptive start index and overflow protecting circuit. The dynamic iSAR may start from the previous conversion level rather than mid-level, and proceed from thereon with a smaller step, at a radix-2 scale index lower than MSB−1 (as shown in FIG. 3*e*, bottom portion). If the sampled input is sufficiently close to the previous conversion level (curves 337, 339 as shown in FIG. 3*e*), then the iSAR's search may continue to successively zoom in with the index stepping down each time the comparator flips, reaching the LSB in a number of cycles typically less than the number of bits, less than needed for conventional SAR systems (including LSB-first SAR ADC). If the input changes from its previous level to a greater extent (e.g., greater in step than the radix-2 scale of the start index), the search may require zoom-out operations to catch up, where the index may undergo upward excursions until the comparator flips to resume a downward settling trend towards the LSB (curves 336, 338, as shown in FIG. 3*e*).

In particular, the iSAR may step up the index (e.g., increase the step size twofold) if and, as long as, the comparator retains the same polarity (and/or the index reaches its maximum at MSB-1), and may step down the index (e.g., decrease the step size twofold) as soon as and whenever the comparator flips polarity (and/or the series terminates when the index reaches its minimum at LSB). The iSAR may further maintain the index when the comparator stays for consecutive cycles at the same polarity. This may slow down the process somewhat and produce more robust convergence in the presence of noise and errors in the comparison. The iSAR may settle in a limit cycle of alternating LSB steps up and down. For the terminal cycle, a downward step may be reverted to recover one bit of precision.

Figure 1:
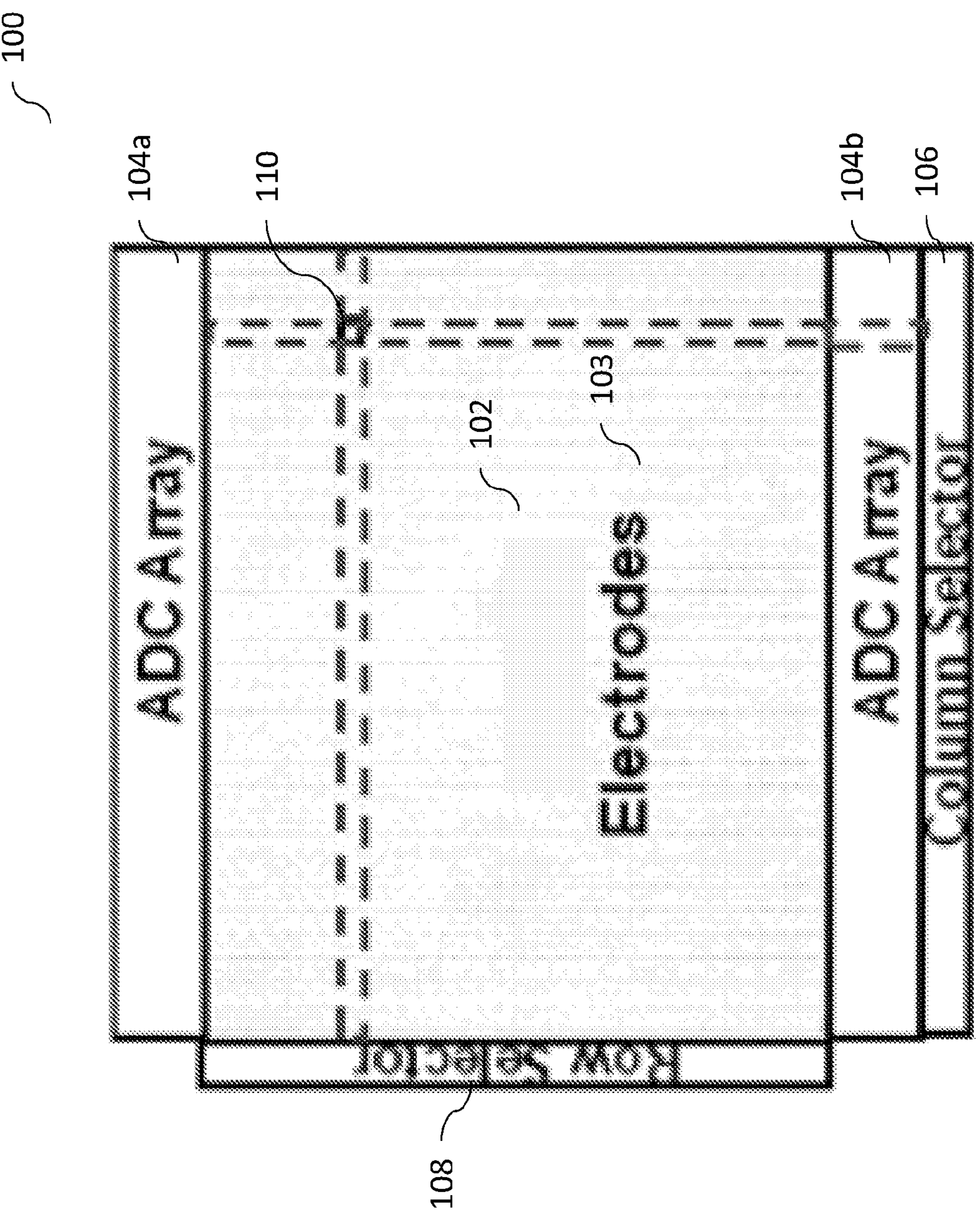
FIG. 1 illustrates an exemplary neural interface system-on-chip, according to some implementations of the current subject matter.
Figure 2A:
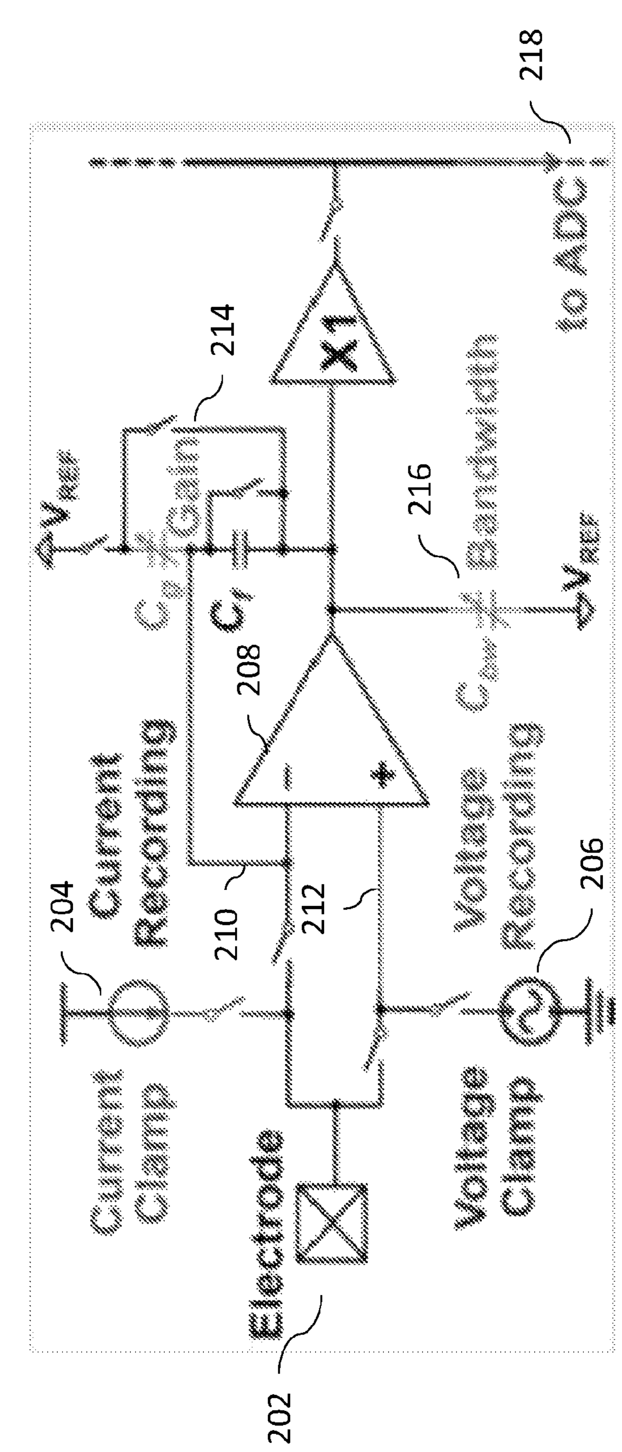
FIG. 2*a* illustrates an exemplary circuitry of one of the analog front ends shown in FIG. 1, according to some implementations of the current subject matter.

In some exemplary, non-limiting implementations, the current subject matter relates to a system and a method for recording of biopotential signals from an array of 1,024 electrodes (e.g., as shown in FIG. 1 and discussed below). An exemplary 32×32 electrode array may be integrated on a 2 mm×2 mm 65 nm complimentary metal-oxide-semiconductor (CMOS) silicon neural interface system-on-chip (NISoC). The NISoC may include an array of 32 column-parallel iSAR ADCs for on-chip digitization, which may cover an entire frequency range of neural biopotentials from LFPs to action potentials. The NISoC may also provide configurable spatially patterned simultaneous electrical stimulation capability. The NISOC may support voltage and current clamping through a programmable interface (e.g., as shown in FIG. 2*a* and discussed below). Global control variables may be used to configure gain and/or bandwidth for either voltage and/or current recording, thereby generating a proportional voltage output. One 12-bit iSAR ADC may, for example, digitize the 32 outputs in a column.

Further, the iSAR may be configured to implement one or more components of conventional SAR. It may also include a pre-settable indexed up/down counter (rather than a standard register), and an additional index control logic (e.g., as shown in FIG. 3*a* and discussed below). The control logic may include an overflow protection avoiding the register to exceed the DAC range, otherwise causing DAC charge loss. The iSAR may include a frame memory buffer to store and/or recall 1,204 previous output values for preload. In some exemplary implementations, the on-chip integration of a 12 k-bit buffer may provide substantial energy savings.

As stated above, in some implementations, the current subject matter may be configured to provide a neural interface that may be used to "merge" one or more characteristics of a human brain and a machine by establishing a bidirectional communication between artificial neuron(s) and biological neuron(s). This may be accomplished by one or more tools that may be capable of recording and stimulating biological neurons, such as, for example, patch clamp system with glass probes and a planar multi-electrode array (MEA). The current subject matter's mobile and/or implantable system-on-chip may provide an integrated neural interface that may offer simultaneous current recording and/or voltage recoding and/or stimulation capabilities, which may be essential to characterize ion currents through membranes, as well as voltammetry to measure redox currents from neurotransmitter electrochemical activity, etc. Moreover, the neural interface system-on-chip may be configured to detect/measure one or more signals on one or more signal channels and determine corresponding signal impedance on that channel, whereby a signal channel with the lowest impedance may be selected for an improved signal quality. The impedance on that channel may be determined by periodically either current clamping and/or voltage clamping the electrode and registering the corresponding signal change. Further, the current subject matter's system-on-chip may offer a reduced physical size and/or power consumption.

In some exemplary, non-limiting implementations, the neural interface system-on-chip may be configured for measurement of one or more signals during at least one of the following procedures: an electroencephalography (EEG), an ear-electroencephalography (ear-EEG), an electrocardiography (ECG), an electrooculography (EOG), and/or any other procedures and/or any combination thereof. Further, the neural interface system-on-chip may also be configured for at least one of the following: a seizure detection, a seizure forecasting, a detection of an inter-ictal discharge (IED) biomarker, an analysis of internal carotid artery (ICA), and any combination thereof. The above procedures may be performed on a subject (e.g., a patient, a user, etc.) at any desired location (e.g., hospital, medical office, laboratory, clinic, ambulatory setting, home setting, etc.). Moreover, in some exemplary, non-limiting, implementations, the neural interface system-on-chip may include and/or otherwise be coupled to one or more computing components (e.g., one or more processors, memory(ies), communication components, etc.) that may include one or more of hardware and/or software that may be used for the purposes of receiving/transmitting programming commands, storing various data (e.g., signal data, voltage data, current data, impedance data, etc.), receiving data, transmitting data, and/or used for any other purposes.

FIG. 1 illustrates an exemplary neural interface system-on-chip 100, according to some implementations of the current subject matter. The system 100 may be configured to include one or more analog front ends 102 coupled to one or more electrodes 103 and one or more analog-to-digital (ADC) converters 104. In some exemplary implementations, the system 100 may be disposed on a substrate (not shown in FIG. 1). Each front end 102 may be configured to function as both a current-clamp and/or a voltage-clamp. Each ADC 104 may be configured to be shared by the AFEs 102 in one column. As shown in FIG. 1, the system 100 may include a first ADC array 104*a* and a second ADC array 104*b*. A column selector component 106 and a row selector component 108 may be configured to select a particular AFE-ADC combination 110. The system 100 may be programmed to achieve a low-energy digitization.

In some exemplary, non-limiting implementations, the system 100 may be configured as a 2 mm×2 mm on a 65 nm substrate that may integrate 1024 analog front-ends 102 and 32 analog-to-digital converters 104. Thus, each ADC 104 may be shared by 32 AFE in one column.

FIG. 2*a* illustrates an exemplary circuitry of one of the analog front ends 102 shown in FIG. 1, according to some implementations of the current subject matter. The AFE 102 may include an electrode 202, a current clamp/stimulator component 204, a voltage clamp/stimulator component 206, an amplifier (e.g., a non-inverting gain amplifier) 208, a gain component 214, and a bandwidth component 216. The AFE 102 may be coupled to an ADC 104 (not shown in FIG. 4) via a connection 218.

In some exemplary implementations, the current clamp/stimulator component 204 may be configured as a cascoded current mirror. The voltage clamp/stimulator component 206 may be implemented with one or more (e.g., two) voltage sources. The amplitude and/or polarity of current and voltage stimulators 204, 206 may be globally programmable. The amplifier 208 may be configured to measure voltage (e.g., via branch 212) and/or configured as an integrator to measure current (e.g., via branch 210). The voltage and/or current sensing mode of the amplifier 208 may be configured through one or more low leakage switches (not shown in FIG. 2*a*), the timing of which may also be used to implement correlated double sampling of the voltage and/or current signal. For instance, the high current bias may only be enabled when sampling happens, which may substantially reduce power consumption. The gain component 214 and/or bandwidth component 216 may be controlled by connecting and/or disconnecting one or more select capacitors.

Figure 2B:
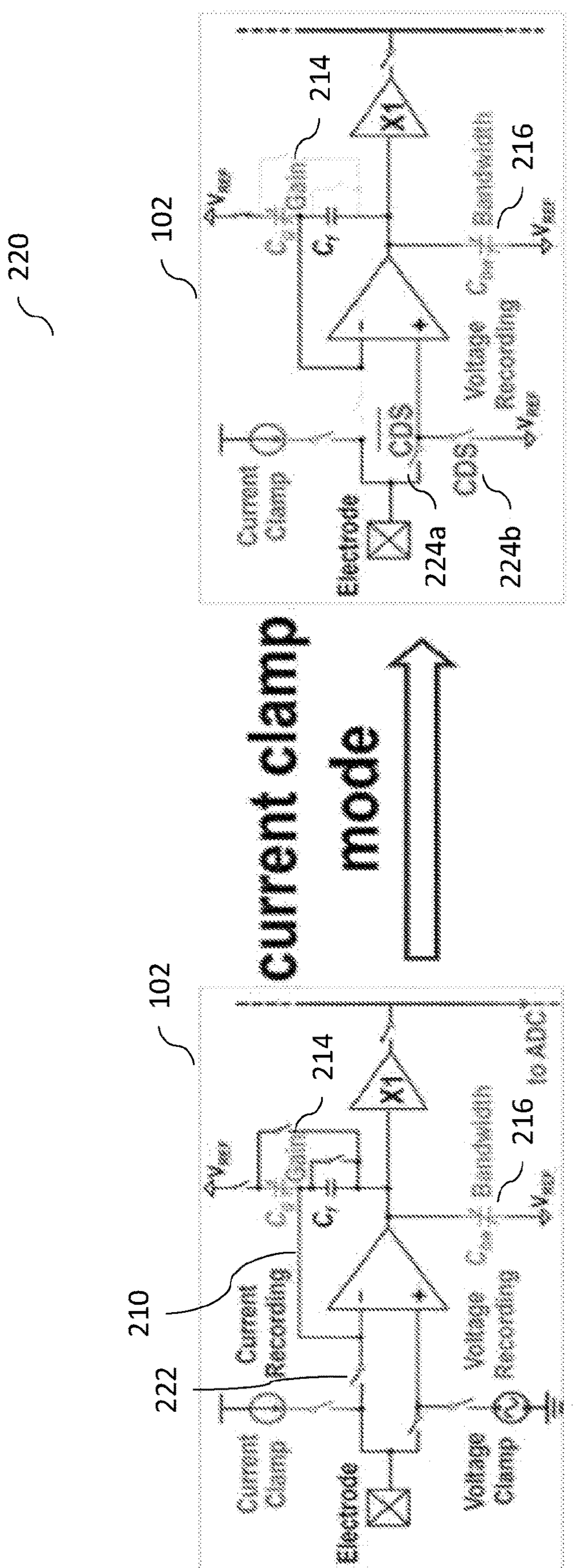
FIG. 2*b* illustrates an exemplary analog front end's current clamp mode, according to some implementations of the current subject matter.

FIG. 2*b* illustrates an exemplary analog front end's current clamp mode 220, according to some implementations of the current subject matter. In the current clamp mode 220, cell membrane potential may be recorded by injecting current into a cell through the recording electrode. This is different from the voltage clamp mode, where the membrane potential is held at a predetermined level. In the current clamp mode, the membrane potential may vary, whereby the amplifier may records whatever voltage the cell may generates on its own and/or as a result of stimulation. This mode may be used to determine how a cell responds when electric current enters a cell (e.g., how neurons respond to neurotransmitters that act by opening membrane ion channels).

Referring back to FIG. 2*b*, the AFE 102 may be used to measure voltage through branch 212. To do so, one or more switches 222 may be turned off (e.g., globally turned off), and thus, branch 210, to thereby make front end function as a non-inverting amplifier. A correlated double sampling (CDS) 224(*a, b*) may be implemented to remove offset drift and reduce low frequency noise. The gain may be determined by a ratio of capacitances, and may be digitally programmed by selecting one or more gain capacitors $C_g$ that may be incorporated into the gain component 214 along with capacitor(s) $C_f$. The programmable gain may be expressed using the following relationship $(C_g+C_f) C_f$. Similarly, bandwidth may be tuned by selecting among a bank of loading capacitors $C_{bw}$ that may be incorporated into the bandwidth component 216.

Figure 2C:
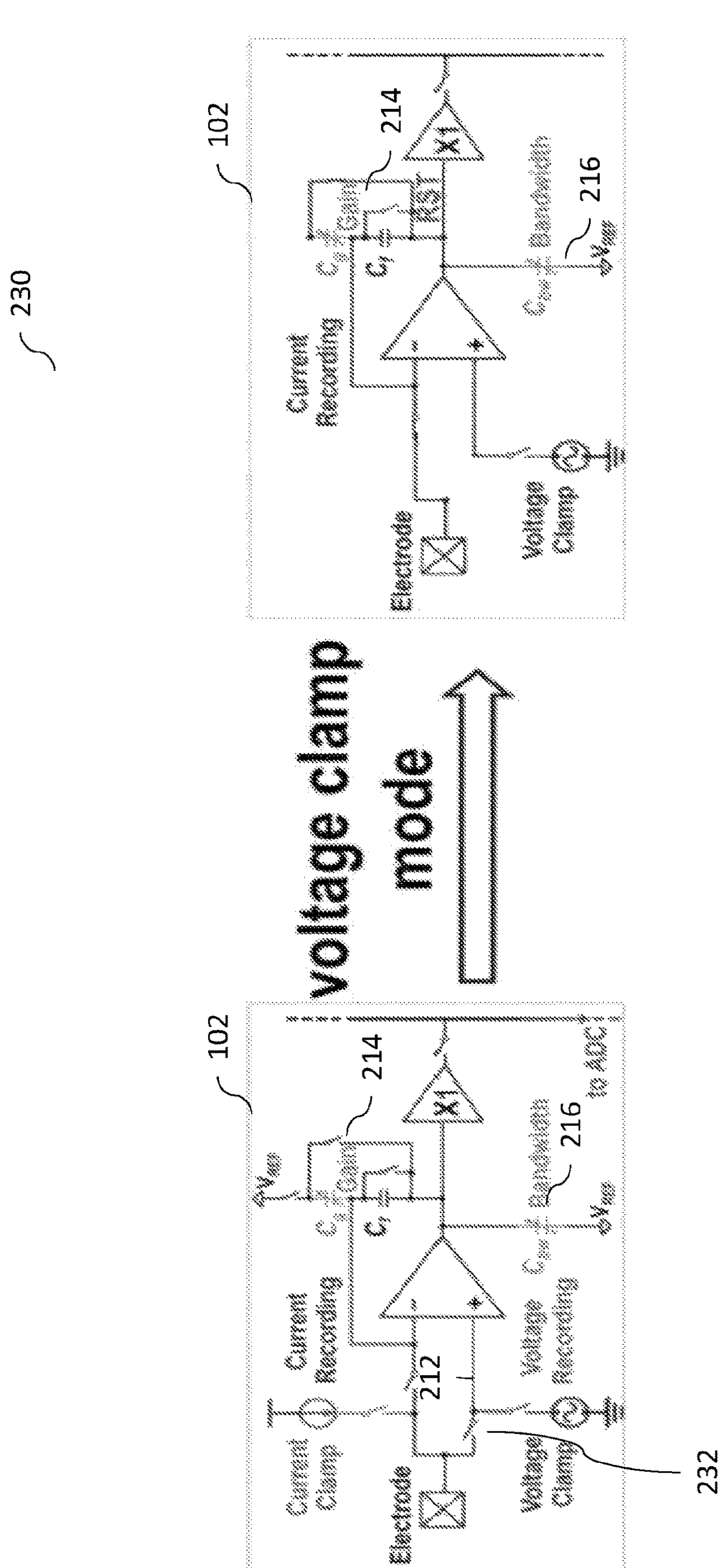
FIG. 2*c* illustrates an exemplary analog front end's voltage clamp mode, according to some implementations of the current subject matter.

FIG. 2*c* illustrates an exemplary analog front end's voltage clamp mode 230, according to some implementations of the current subject matter. In the voltage clamp mode 230, the system 100 (shown in FIG. 1) may be configured to measure ion currents passing through the membranes of excitable cells, such as neurons, while holding the membrane voltage at a set level. In this mode, one or more of the switches 232 may be turned off (and thus, branch 212) to thereby make front end function as an integrator to measure current through current branch 210. In this mode, the current gain may be digitally programmable by configuring integration time (Δt) and value of integration capacitor ($C_g$) of the gain component 214. The gain may be expressed as follows:

$$I = \frac{\Delta Q}{\Delta t} = \frac{\Delta V}{\Delta t}(C_g + C_f) \quad (1)$$

In voltage clamp mode 230, the system 100 may be configured to measure current from, for example, tens of fA to tens of nA. Self-calibration of stimulation currents, for charge-balanced stimulation, may be implemented by recording current directly from the current stimulator.

FIG. 3*a* illustrates an exemplary on-chip analog to digital converter(s) 104 shown in FIG. 1, according to some implementations of the current subject matter. The ADC 104 may be configured to include a sample-and-hold circuit component 302, an amplifier 304, a bin-to-thermometer binary converter 306, an indexed up/down counter 308, and control logic 310 that may supply index value(s) 312 and up/down value(s) 314. A voltage $V_{amp}$ 316 may be supplied from the electrode column (as shown in FIG. 1). The on-chip ADCs (e.g., 32 ADC as shown in FIG. 1) may be configured to operate in the following modes: a successive approximation register mode (SAR) and a dynamic incremental SAR (iSAR) mode.

The sample and hold circuit 302 may be an analog device that may sample voltage of a continuously varying analog signal and hold its value at a constant level for a specified minimum period of time. This circuit may be used to eliminate variations in input signal that can corrupt conversion process. The circuit 302 may store electric charge in a capacitor and may include at least one switching device and an operational amplifier. To sample the input signal the switch may connect the capacitor to the output of a buffer amplifier. The buffer amplifier may charge and/or discharge the capacitor so that the voltage across the capacitor is substantially equal, and/or proportional to, input voltage. In a hold mode, the switch may disconnect the capacitor from the buffer.

In a conventional SAR ADC, a sample and old circuit may be configured to acquire an input voltage, compare it to an internal DAC and output the result of the comparison to SAR. The SAR may supply an approximate digital code of the input voltage to the internal DAC. The DAC may supply an analog voltage equal to the digital code output of the SAR to the comparator for comparison with a reference voltage (e.g., $V_{ref}$). The conventional SAR may be initialized so that the MSB is equal to 1. This code is fed into the DAC, which then supplies the analog equivalent of this digital code ($V_{ref}/2$) into the comparator for comparison with the sampled input voltage. If this analog voltage exceeds the input voltage, then the comparator causes the SAR to reset this bit; otherwise, the bit is 1. The next bit may be set to 1 and the comparison may be performed again, thereby continuing a binary search until all bits in the SAR has been tested. The resulting code is the digital approximation of the sampled input voltage and is finally output by the SAR at the end of the conversion.

In some implementations, the current subject matter may incorporate the counter 308 that may be a pre-settable indexed up/down counter as opposed to a conventional standard register. The index control logic 310 may include an overflow protection to avoid the register to exceed the DAC range, which otherwise may cause DAC charge loss. Using the counter 308, whether the ADC 104 is operating in the SAR or iSAR mode, the conversion process may be used to make the voltage difference between the sampled input and the DAC converge to zero, by updating DAC digital value.

As shown in FIG. 3*a*, the voltages supplied to the comparator 304, may be expressed as follows:

$$V_- = V_{DAC} - V_{amp} + V_{CM} \quad (2)$$

$$V_+ = V_{CM}$$

whereby $V_+ - V_- = V_{amp} - V_{DAC}$

The DAC voltage may be determined as follows:

$$V_{DAC} = V_L + \frac{digi}{2^{12}}(V_H - V_L) \quad (3)$$

$$\text{Thus, when } V_H = V_{DD} \text{ and } V_L = 0,\ V_+ - V_- = V_{amp} - \frac{digi}{2^{12}} V_{DD} \quad (4)$$

Further, in some exemplary, non-limiting implementations, the iSAR may require a frame memory buffer to store and recall 1,024 previous 12-b output values for preload in sequential scanned order. One of the advantages of the iSAR is that the memory may consume a negligible silicon area by the on-chip integration of a 12-kb buffer while affording substantial energy savings.

FIG. 3*b* illustrates an exemplary plot 320 illustrating a search path for a SAR operating mode. In particular, the plot 320 shows a sequential SAR operation process, where, starting from a middle of the range, the search may repeatedly zoom in by a factor 2 until all bits are determined. The step size may be defined as $2^{index}$. The index may decrease by 1 from MSB−1. Thus, the step size may be divided by 2.

Figure 3C:
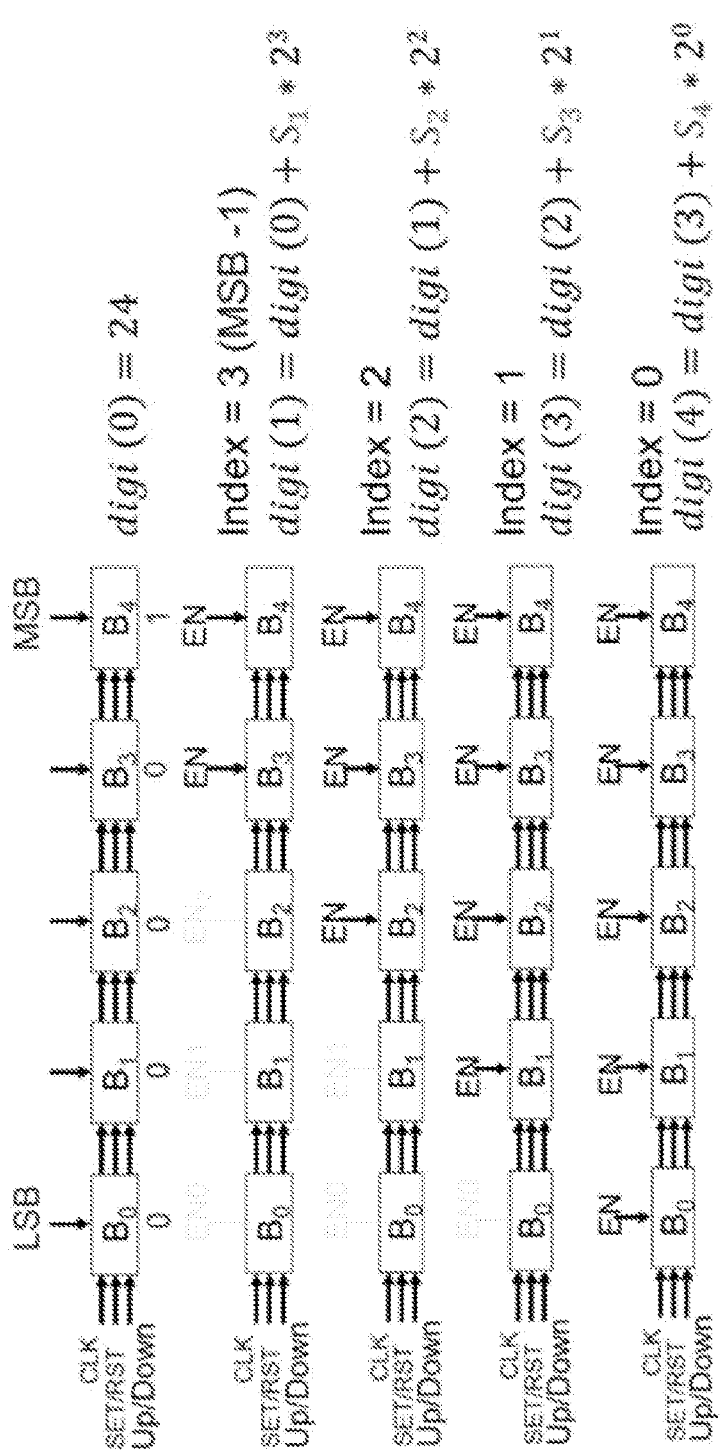
FIG. 3*c* illustrates operation of the ADC in the SAR mode.

FIG. 3*c* illustrates operation 325 of the ADC in the SAR mode. In particular, for ease of illustration, FIG. 3*c* shows an exemplary 5-bit ADC (i.e., bits $B_0$, $B_1$, $B_2$, $B_3$, $B_4$, where $B_0$ being the least significant bit and $B_4$ being the most significant bit). Since it is a 5-bit ADC, the decision bits $S_n$ may be determined using the following:

$$V_{amp} - \frac{digi(n-1)}{2^5} V_{DD}.$$

In the first cycle, the counter 308 (as shown in FIG. 3*a*) may be initialized to its mid-range, e.g., 10000 (i.e., digi(0)=24). Then, the index may be set to MSB−1, which for a 5-bit ADC is 3. This value of the index may disable the three least significant bits of the counter (i.e., $B_0$, $B_1$, $B_2$) and enable (EN) the remaining bits. These bits may continue to hold their respective values. The 2-bit enabled counter may go up or down by a step of $2^{index}$, depending on the comparison result of cycle 1. During the next cycle, the index may decrease by 1, and the 3-bit enabled counter may go up or down depending on the previous comparison result. This procedure may be repeated until the LSB is determined, as shown by the equations in FIG. 3*c* corresponding to each step.

Figure 3D:
FIG. 3*d* illustrates operation of the ADC in the iSAR mode, according to some implementations of the current subject matter.
Figure 3D:
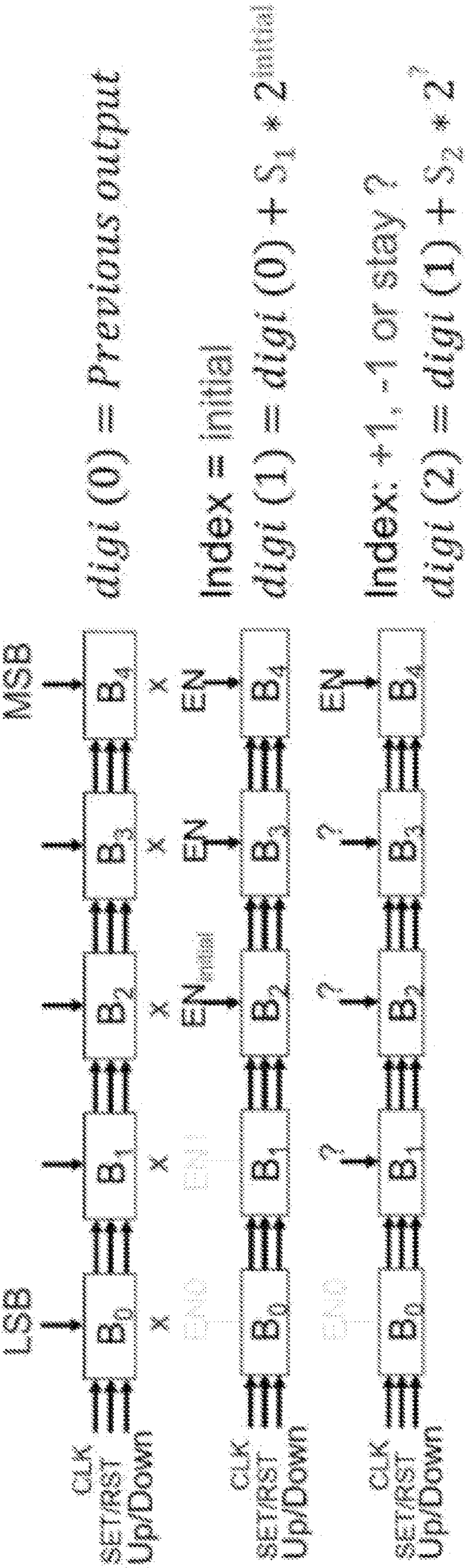
Figure 3E:
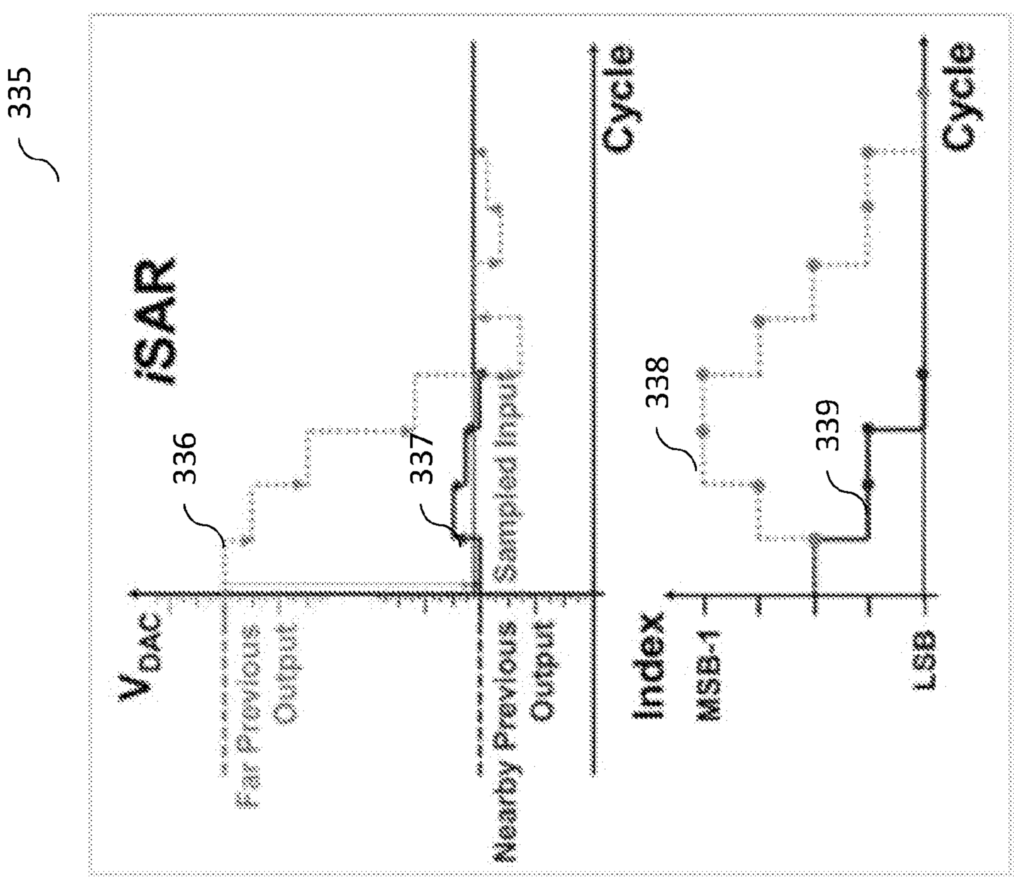
FIG. 3*e* illustrates an exemplary plot illustrating a search path for an iSAR operating mode shown in FIG. 3*d* (i.e., for a 5-bit ADC), according to some implementations of the current subject matter.

FIG. 3*d* illustrates operation 330 of the ADC in the iSAR mode, according to some implementations of the current subject matter. Again, for ease of illustration, a 5-bit ADC (similar to the 5-bit ADC shown in FIG. 3*c*) is shown. The operation 330 proceeds as follows. First, the counter 308 (shown in FIG. 3*a*) may be initialized to the previous conversion value, instead of the mid-range, as in the case of the SAR operation mode 325 shown in FIG. 3*c*. The bits $S_n$ may be determined in a similar way as for the operation 325, however, the sequence of indices/index is no longer descending from MSB to LSB. In the first cycle, the index may be set to an initial value (e.g., digi(1)=digi(0)+$S_1*2^{initial}$, where digi(0) represents previous output). This value may be programmable. In the following cycles, the iSAR may allow index variation by at most one unit each cycle, based on the history of decision bits $S_n$. Thus, during operation of the iSAR operates, the index may be increased (i.e., "+1") every cycle until $V_{DAC}$ crosses $V_{amp}$ and after that, the index may be decreased (i.e., "−1") only when comparator flips output/sign, otherwise the index is unchanged.

FIG. 3*e* illustrates an exemplary plot 335 illustrating a search path for an iSAR operating mode shown in FIG. 3*d* (i.e., for a 5-bit ADC), according to some implementations of the current subject matter. Here, the maximum step is $(V_H+V_L)/4$ since maximum index is MSB−1. As shown in FIG. 3*e*, when the new sample is farther away from the previous one (as shown by curves 336 and 338), the iSAR may first zoom out very step until $V_{DAC}$ crosses $V_{amp}$. Again, the index value may define step size. The index value may start from an initial value and increase by 1 every cycle before $V_{DAC}$ crosses $V_{amp}$, until it reaches maximum value MSB−1. It only decreases when $V_{DAC}$ crosses sampled input.

When the new sample is close to the previous one (as shown by curves 337 and 339 in FIG. 3*e*) (e.g., closer than $2^{initial}$ index), the iSAR may be configured to converge quickly, with the index only going down towards the LSB. The iSAR may go down just for every crossing, which is more robust to comparator error. This may allow for error correction and overflow protection.

As shown in FIGS. 3*b* and 3*e*, the SAR search path (shown in FIG. 3*b*) requires N cycles per conversion for an N bit resolution. The number of cycles for the iSAR search path may depend on its signal slope. Thus, for typical neural signals of interest, the signal does not vary much between samples except during short transients, so that on average much fewer than N cycles may be required for an N bit resolution. The iSAR's fast convergence for slow signals does not make any assumptions on the signal amplitude itself (i.e., amplitude independent), unlike LSB-first SAR, which may require more than 12 cycles even for some very nearby sample. Thus, as stated above, a further advantage of the iSAR is that it may correct errors due to DAC and comparator noise.

Figure 4:
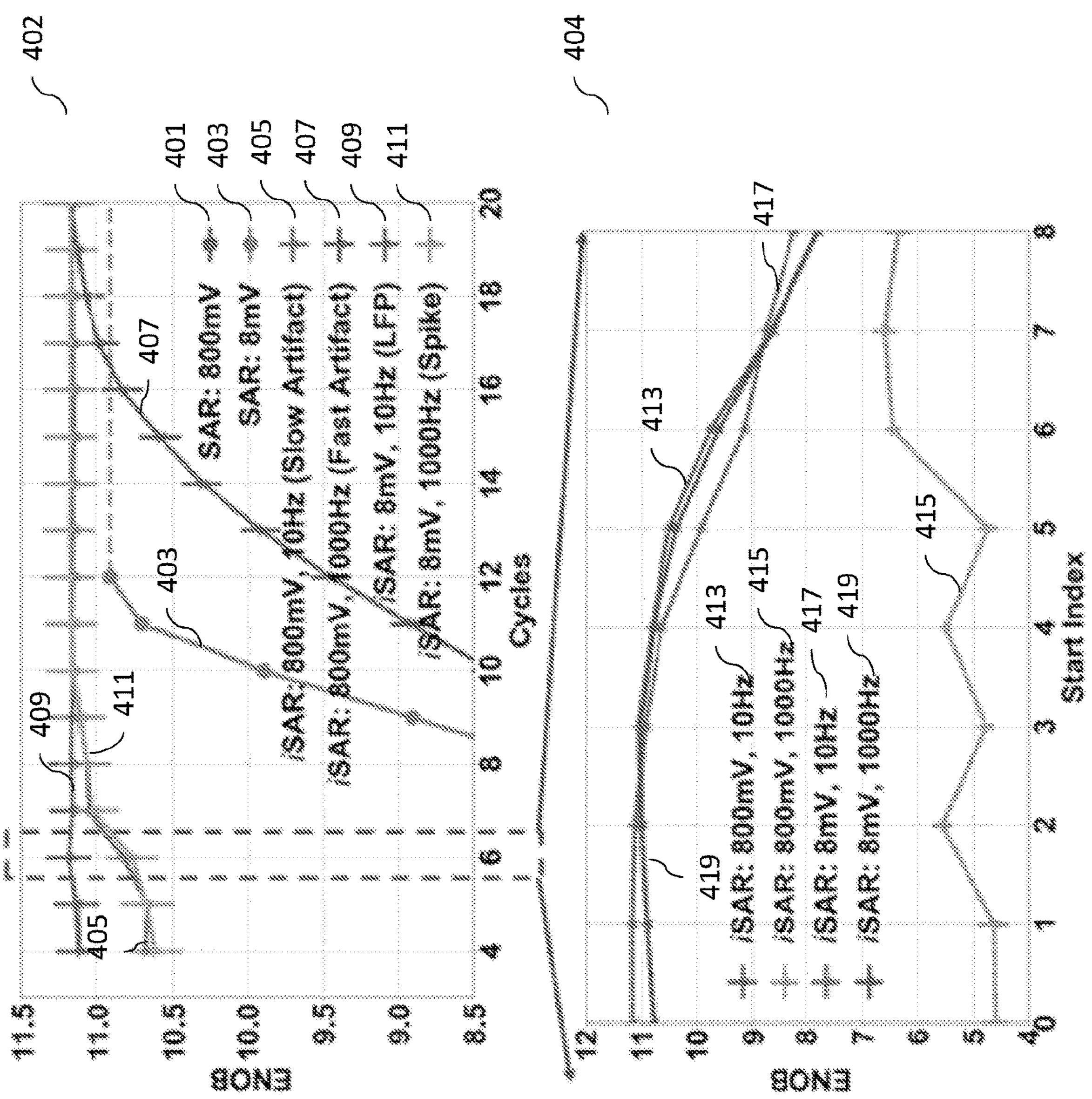
FIG. 4 illustrates exemplary plots showing an effective number of bits (ENOB) for conventional SAR and incremental SAR (iSAR) ADC, as shown in FIG. 1.

FIG. 4 shows a measured performance of one column ADC configured in SAR and iSAR modes, as a function of the number of cycles (successive approximation steps). iSAR requires choice of start index, the optimal value of which is signal dependent but can be dynamically tuned by tracking average peak consecutive level differences in the signal. For slowly varying signals, iSAR reaches higher effective number of bits (ENOB) than SAR (11.2 rather than 10.9), in less than half the number of cycles (fewer than 6 rather than 12). ENOB is defined here as the effective number of bits of the ideal quantizer producing the same SNDR as the measured output at the signal input level. In particular, FIG. 4 illustrates exemplary, experimental ENOB versus cycles plot 402 and ENOB-start-index plot 404. The ENOB may be determined based on signal to (noise+distortion) (SNDR) using the following equation:

$$ENOB = \frac{SNDR - 1.76\ \text{dB}}{6.02\ \text{dB}} \qquad (5)$$

In particular, the plots 402, 404 illustrated measured ENOB for the ADC in SAR and iSAR modes for different neural signals. As shown in FIG. 4*a*, the plot 402 illustrates measured ENOB in relation to the number of cycles for SAR with signal voltage 800 mV (curve 401) and 8 mV (curve 403). By comparison, the ENOB for the iSAR are shown for signal voltage 800 mV, 10 Hz (slow artifact) (curve 405), 800 mV, 1000 Hz (fast artifact) (curve 407), 8 mV 10 Hz (LFP) (curve 409), and 8 mV 1000 Hz (spike) (curve 411).

Plot 404 shows curves for measured ENOBs in relation to the start index for the iSAR. Specifically, curve 413 represents the measured ENOB for the iSAR with signal voltage 800 mV, 10 Hz; curve 415—800 mV, 1000 Hz; curve 417—8 mV 10 Hz; and curve 419—8 mV 1000 Hz.

It should be noted that the 12-bit SAR ADC achieves its optimal 11-b ENOB in 12 cycles (curves 401-403) independent of the input signal. However, as shown in FIG. 4, the ENOB of the iSAR may be input signal slope dependent and achieves 11 ENOB in approximately 6 cycles for all signals of interest (curves 405-411).

Figure 5:
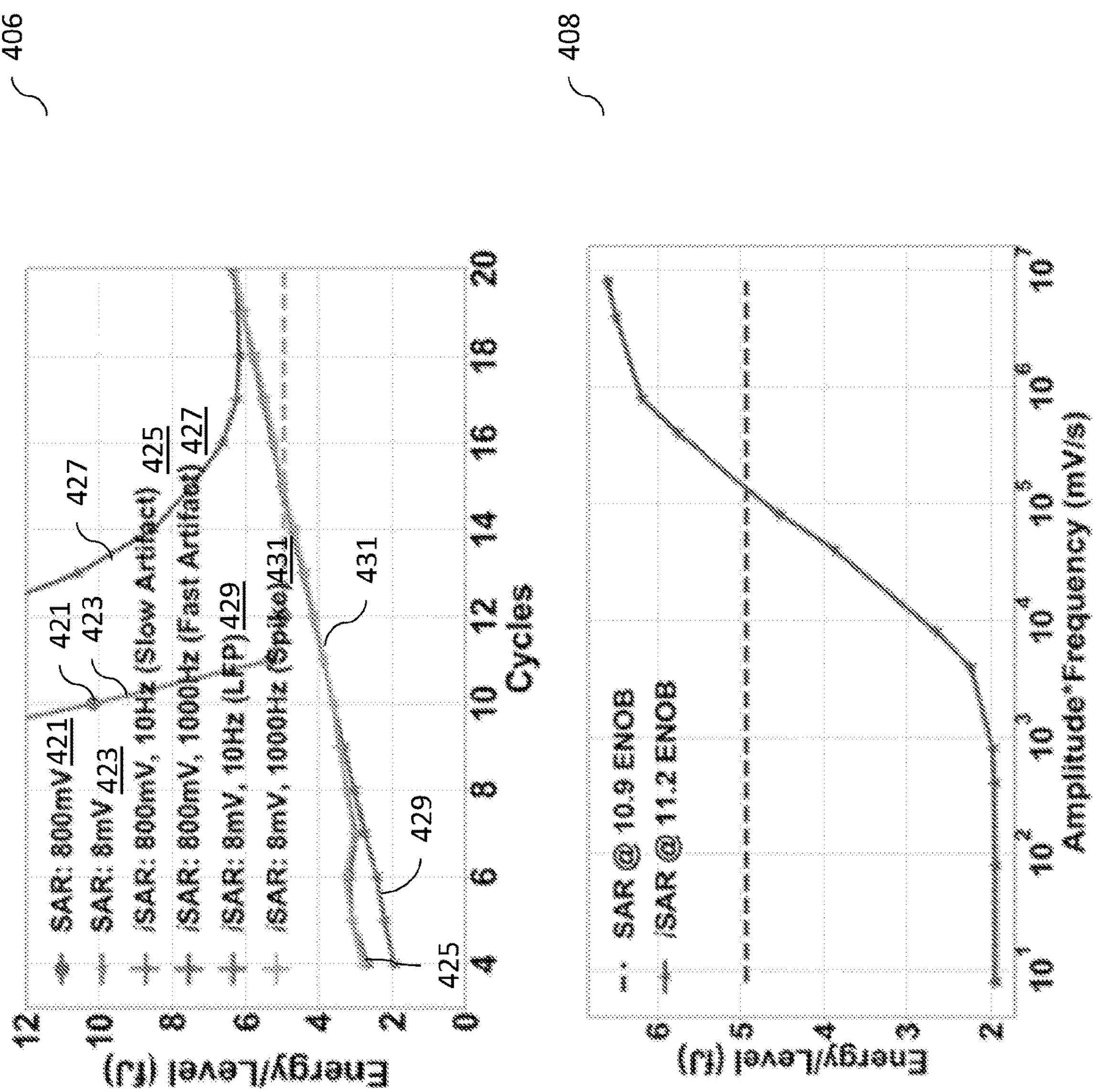
FIG. 5 illustrates exemplary plots showing energy efficiency figure-of-merit (FOM) for conventional SAR and incremental SAR (iSAR) ADC, as shown in FIG. 1.

FIG. 5 shows the corresponding energy efficiency figure-of-merit (FOM), as the measured ADC energy per conversion level at ENOB. As SAR energy per conversion is almost directly proportional to the number of cycles, the iSAR reaches an ADC FOM more than twice lower than SAR (2 fJ/level rather than 5 fJ/level) for signals changing slower than 1 mV/ms, typical of LFP, ECoG, dopamine, and other biopotential and electrochemical neural signals. Changes in these signals are frequently limited to a few levels only, so that a few cycles of LSB-level iSAR iteration help to boost signal-to-noise ratio beyond the quantization level.

In particular, FIG. 5 illustrates exemplary experimental plots 406 and 408 representing energy/level (fJ) in relation number of cycles (plot 406) and amplitude*frequency (mV/s) (plot 408). As shown in the plots, the energy/level may depend on the signal slope, whereby a substantial amount of energy (e.g., 60%) may be saved for neural signal recording. The plots 406 and 408 illustrate experimental measurements for the same SAR and iSAR combinations shown in FIG. 4*a*, i.e., SAR signal voltage 800 mV (curve 421), SAR 8 mV (curve 423), iSAR 800 mV, 10 Hz (slow artifact) (curve 425), 800 mV, 1000 Hz (fast artifact) (curve 427), 8 mV 10 Hz (LFP) (curve 429), and 8 mV 1000 Hz (spike) (curve 431).

Figure 6:
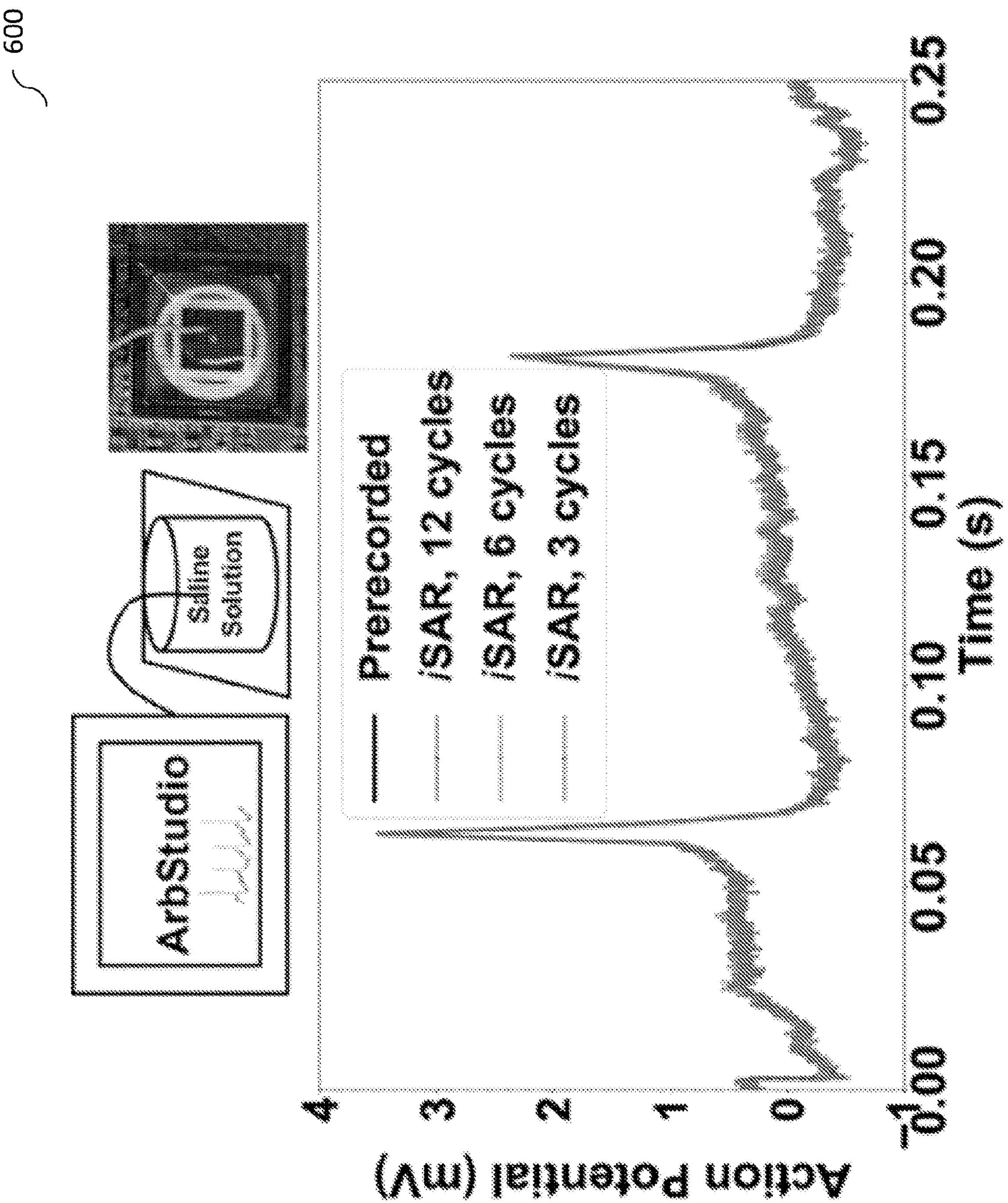
FIG. 6 illustrates an exemplary plot showing recording of regenerated spike neural data presented through saline in contact with the electrodes, for different number of iSAR cycles per conversion, according to some implementations of the current subject matter.

FIG. 6 illustrates an exemplary plot 600 illustrating experimental validation of the operational capabilities of the NISoC. For this validation, pre-recorded spike data from a leech ganglion neuron was played back on a voltage generator and the signal was applied to an electrode immersed in a saline solution in contact with the on-chip electrodes. As shown in FIG. 6, recording of pre-recorded spike data from a leech ganglion neuron, reconstituted to original amplitude and presented through an external electrode immersed in saline within an epoxy seal ring over the exposed depassivated top-metal electrode array, yields accurate reconstruction through the analog front-end (with gain 60) and ADC back-end even down to 3 iSAR cycles per conversion (as shown in FIG. 6).

In some exemplary, non-limiting implementations, as stated above, the current subject matter may be configured as a neural interface system-on-chip (NISoC) with 1,024 channels of simultaneous electrical recording and stimulation for high-resolution, high-throughput electrophysiology. The exemplary experimental implementation may include a 2 mm×2 mm NISoC in 65 nm CMOS that integrates a 32×32 array of electrodes. The electrodes may be vertically coupled to analog front-ends supporting both voltage and current clamping through a programmable interface, which may range over 100 dB in voltage and 120 dB in current, with 0.82 μW power per channel at 5.96 μl/rms input-referred voltage noise from DC to 12.5 kHz signal bandwidth. This may include on-chip acquisition with a back-end array of 32 dynamic incremental SAR ADCs for 25 Msps 11-ENOB acquisition at 2 fJ/level FOM.

Current and voltage clamp functions may be activated by one or more analog switches controlled by local state variables based on local ternary coefficient and global signal waveform. Non-inverting voltage and integrating current amplification may share a single folded double-cascode OTA (94 dB open-loop DC gain at 500 nA bias) with configurable capacitive feedback for gain and bandwidth control through global control variables. Analog switches directly in contact to the integrating node may be centrally bulk-source connected for ultra-low leakage extending integration time for fA-range current acquisition. Unity gain, low-input capacitance buffering of the voltage output may be dynamically biased synchronous with time-multiplexed readout for substantial power savings with negligible kick-back noise. Measured voltage gain, bandwidth, and input-referred noise (gain (G)=60) as a function of frequency are illustrated in FIG. 4.

Figure 7:
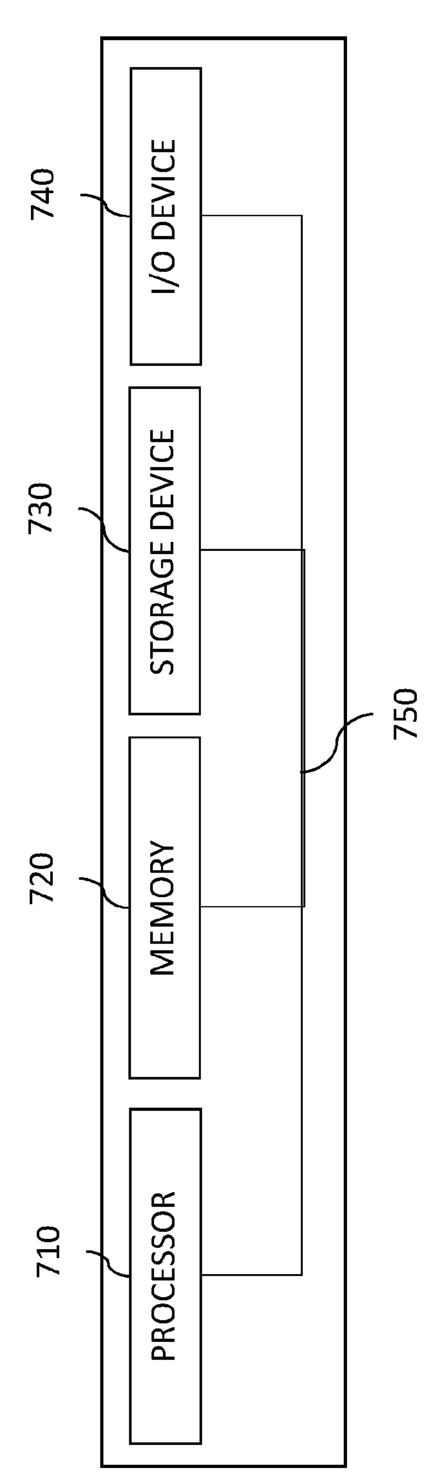
FIG. 7 illustrates an exemplary system, according to some implementations of the current subject matter.

In some implementations, the current subject matter can be configured to be implemented in a system 700, as shown in FIG. 7. The system 700 can include a processor 710, a memory 720, a storage device 730, and an input/output device 740. Each of the components 710, 720, 730 and 740 can be interconnected using a system bus 750. The processor 710 can be configured to process instructions for execution within the system 700. In some implementations, the processor 710 can be a single-threaded processor. In alternate implementations, the processor 710 can be a multi-threaded processor. The processor 710 can be further configured to process instructions stored in the memory 720 or on the storage device 730, including receiving or sending information through the input/output device 740. The memory 720 can store information within the system 700. In some implementations, the memory 720 can be a computer-readable medium. In alternate implementations, the memory 720 can be a volatile memory unit. In yet some implementations, the memory 720 can be a non-volatile memory unit. The storage device 730 can be capable of providing mass storage for the system 700. In some implementations, the storage device 730 can be a computer-readable medium. In alternate implementations, the storage device 730 can be a floppy disk device, a hard disk device, an optical disk device, a tape device, non-volatile solid state memory, or any other type of storage device. The input/output device 740 can be configured to provide input/output operations for the system 700. In some implementations, the input/output device 740 can include a keyboard and/or pointing device. In alternate implementations, the input/output device 740 can include a display unit for displaying graphical user interfaces.

In some implementations, the current subject matter relates to a system for recording neural signals (e.g., of a user's brain, etc.). The system (e.g., the system 100 as shown in FIG. 1) may include one or more electrodes (e.g., electrodes 103, as shown in FIG. 1) coupled to one or more corresponding analog front end components (e.g., AFEs 102, as shown in FIG. 1). The system may also include one or more analog to digital converter components (e.g., ADCs 104) coupled to the one or more electrodes. The electrodes, the analog front end components and the analog to digital converter components may be configured to form a neural interface system-on-chip for recording one or more neural signals.

In some implementations, the current subject matter may include one or more of the following optional features. The electrodes may be integrated on a complimentary metal-oxide-semiconductor integrated circuit. The analog front end components may be configured to be programmable for recording the one or more neural signals. In some exemplary, non-limiting implementations, the electrodes may be vertically coupled to the corresponding analog front end components.

In some implementations, the analog front end components may be configured to operate in at least one of the following programmable modes: a voltage clamp mode (e.g., as shown in FIG. 2*c*) and a current clamp mode (e.g., as shown in FIG. 2*b*). In the voltage clamp mode, the analog front end components may be configured to record one or more currents passing from the corresponding electrodes. By way of a non-limiting example, the currents may be associated with one or more ion currents configured to pass through one or more neural cells. In the current clamp mode, the analog front end components may be configured to record one or more voltage signals on the corresponding one or more electrodes. By way of a non-limiting example, the voltage signals may be generated by one or more neural cells after application of current to the neural cells.

In some implementations, the analog to digital converter components may be configured to perform digital conversion of one or more analog signals received from the analog front end components. Each analog to digital converter component may be configured to support a plurality of analog front end components.

In some implementations, the analog to digital converter components may include a sampling component (e.g., sampling circuit 302 as shown in FIG. 3*a*), a counter component and index component (e.g., circuit 308 as shown in FIG. 3*a*). The analog to digital converter components may be configured to operate using at least one of the following modes: a successive approximation register mode (e.g., as shown in FIGS. 3*b-c*) and an incremental successive approximation register mode (e.g., as shown in FIGS. 3*d-e*). In the successive approximation register mode, the index component of the analog to digital converter components may be configured to determine a least significant bit index value. The least significant bit index value may be determined based on a sampling of one or more input signals to the analog to digital converter components by the sampling component. The sampling may be performed using a plurality of sampling cycles. During each cycle in the plurality of cycles, the counter component may be configured to change a counter value based on an index value determined during a preceding sampling cycle in the plurality of cycles until the least significant index value is determined.

In some implementations, during the incremental successive approximation register mode, the index component may be configured to dynamically vary an index value based on a proximity of consecutive samplings of one or more input signals to the analog to digital converter components by the sampling component. The index component may be configured to decrease the index value until the least significant bit index value is determined. The index component may be configured to increase the index value when a digital to analog converter reference voltage value of the analog to digital converter components corresponds to the voltage value of one or more samplings of one or more input signals to the analog to digital converter components by the sampling component.

In some implementations, in at least one of the voltage clamp mode and the current clamp mode, the neural interface system-on-chip may be configured to determine an impedance of one or more signal channels corresponding to one or more electrodes. Further, the neural interface system-on-chip may be configured to select a signal channel with a lowest measured impedance.

In some exemplary implementations, the neural interface system-on-chip may be configured to measure one or more signals during at least one of the following: an electroencephalography (EEG), an ear-electroencephalography (ear-EEG), an electrocardiography (ECG), an electrooculography (EOG), and any combination thereof.

Moreover, in some exemplary implementations, the neural interface system-on-chip may be configured for at least one of the following: a seizure detection, a seizure forecasting, a detection of an inter-ictal discharge (IED) biomarker, an analysis of internal carotid artery (ICA), and any combination thereof.

Figure 8:
FIG. 8 illustrates an exemplary method, according to some implementations of the current subject matter.
Figure 8:
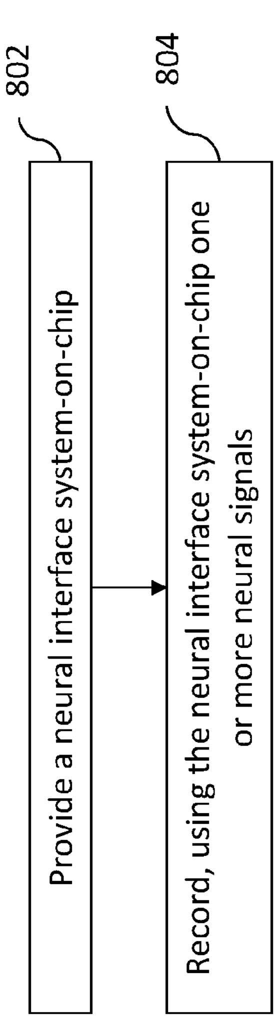

FIG. 8 illustrates an exemplary method 800 for recording neural signals, according to some implementations of the current subject matter. At 802, a neural interface system-on-chip may be provided. The system may include, as discussed above, one or more electrodes integrated on a complimentary metal-oxide-semiconductor integrated circuit and coupled to one or more corresponding analog front end components. The analog front end components may be configured to be programmable for recording one or more neural signals and to operate in at least one of the following selectable programmable modes: a voltage clamp mode and a current clamp mode. The system may further include one or more analog to digital converter components coupled to the electrodes. At 804, using the neural interface system-on-chip, one or more neural signals may be recorded.

As stated above, the neural interface system-on-chip may, for example, be configured for measurement of one or more signals during at least one of the following: an electroencephalography (EEG), an ear-electroencephalography (ear-EEG), an electrocardiography (ECG), an electrooculography (EOG), and any combination thereof. Additionally, the neural interface system-on-chip may also be configured, for example, for at least one of the following: a seizure detection, a seizure forecasting, a detection of an inter-ictal discharge (IED) biomarker, an analysis of internal carotid artery (ICA), and any combination thereof.

In some implementations, the recording may include programming the analog front end components for recording the one or more neural signals.

One or more aspects or features of the subject matter described herein can be realized in digital electronic circuitry, integrated circuitry, specially designed ASICs, field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term “machine-readable medium” refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term “machine-readable signal” refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

Various configurations of an in-ear sensor assembly in which any neural interface system-on-chip described above may be incorporated will now be described in accordance with aspects of the technology.

Figure 9:
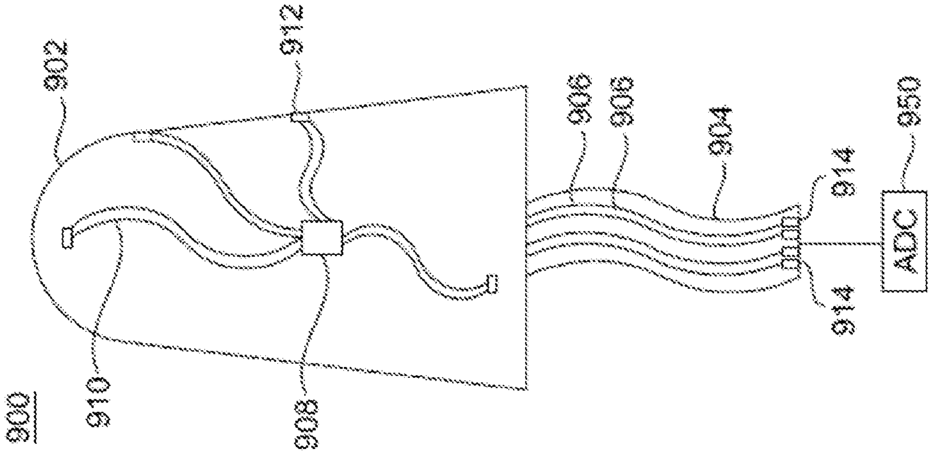

FIG. 9 illustrates an example 900 of an in-ear housing 902 having a flexible printed circuit (FPC) 904 mounted therein, according to some implementations of the current subject matter. The housing 902 may include a foam or otherwise malleable housing that may be compressed for insertion into the ear canal, automatically expanding to contact the ear canal at multiple points. FPC 904 may include multiple conductive wires 906. In some exemplary, non-limiting implementations, the conductive wires 906 may extend within the housing 902 and branch off from a common section (e.g., interface or junction) 908. One or more branches 910 may terminate at a respective electrode 912. Signals detected by the electrodes 912 may be passed to contacts 914 for off-board (remote) processing. The contacts 914 may be operably coupled to an analog-to-digital converter (ADC) 950, which may be similar and/or identical to any of the neural interface system-on-chip embodiments described elsewhere herein. As discussed further below, on-board signal processing and data collection via additional sensors may also be performed by the in-ear sensor assembly. Although FIG. 13A depicts 950 as the ADC, 950 may also include the analog front end 1302 (or one or more of the components of the analog front end), the on-board processing system 1300, or one or more of the components of the on-board processing system 1300.

The conductive wires may be arranged to minimize interference (e.g., cross-coupling) with neighboring wires. In some implementations, the frequencies of interest may be very low (e.g., below 50 Hz), which may minimize cross-talk. A ground plane may be incorporated in the FPC so that the conductive wires may act as transmission lines instead of unshielded wires.

Figure 10:
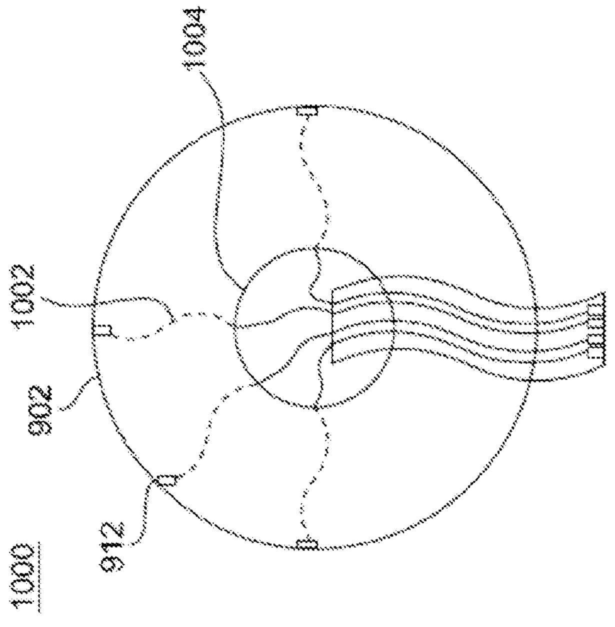
FIGS. 9 and 10 illustrate features of a sensor unit, according to some implementations of the current subject matter.

FIG. 10 illustrates a partial cutaway end view 1000 of the housing 902 and FPC 904, according to some implementations of the current subject matter. The view 1000 is illustrated from the end which will abut a portion of the external auditory canal during use. As shown by dashed lines 1002, the wires of branches 910 may extend at least partly through the housing 902, terminating at the electrodes 912. Also shown in the view 1000 is opening 1004, which may extend longitudinally either substantially and/or completely through the housing 902. The opening 1004 may be configured to pass sound from the external environment through the sensor assembly with little and/or no attenuation and/or distortion. Although only a single opening is depicted, the housing may include a plurality of openings (or channels) as well to carry the audio or sound signals.

The approach in this case may provide an orientation-agnostic in-ear sensor assembly with multiple electrical contacts in, for instance, a ring-type and/or other distributed arrangement as for example, illustrated in FIG. 11 and discussed below. As noted above, while the housing 902 may include foam, other types of materials may be used. In the example of FIGS. 9 and 10, the foam may be non-conductive. Alternatively, or in addition to, other malleable material that may be configured to have conductive regions may be used. Such conductive regions may be arranged so that the electrodes may pass signals through the regions to the FPC. By way of a non-limiting example, carbon particles and/or various other conductive materials (e.g., silver particles) may be added to portions of the malleable material to form one or more conductive regions. For a foam-type arrangement, a conductive coating may be applied to selected portions of the housing's ear-contacting outer surface. The coating may be silver chloride (AgCl) and/or any other conductive material suitable for use with skin-contacting electrodes arranged on a malleable housing.

Figure 11:
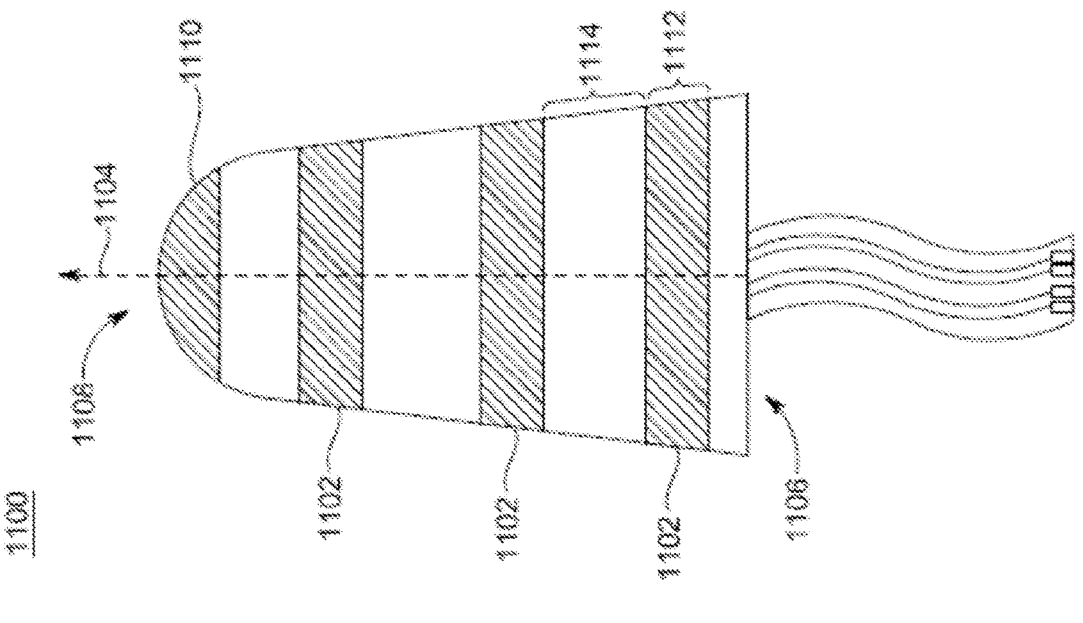
FIG. 11 illustrates an example sensor unit, according to some implementations of the current subject matter.

FIG. 11 illustrates an example electrode arrangement 1100 using a series of conductive rings 1102, according to some implementations of the current subject matter. As shown in FIG. 11, the conductive rings 1102 may be positioned on the exterior surface of the housing. The rings may be spaced apart along the longitudinal axis 1104 of the sensor assembly between a first end 1106 and a second end 1108. The first end 1106 may correspond to the end that may abut a portion of the external auditory canal during wear. The second end 1108 may be arranged closest to the tympanic membrane (e.g., ear drum) upon insertion. Each ring 1102 may be associated with a corresponding electrode connector (not shown in FIG. 11) to provide separate sensed signals to the on-board and/or off-board processing system. Also shown in FIG. 11 is another conductive element 1110 that may be disposed along the second end 1108, which may be associated with its own electrode connector (not shown in FIG. 11). The conductive element 1110 may have a different shape from the rings 1102, such as arcuate, hemispherical, semicircular, circular and/or any other geometric shape.

As can be understood, the number and/or spacing of the rings may vary. In some exemplary implementations, as many rings as possible may be provided so long as the rings do not short one another and/or generate interfering signals, and are able to obtain reliable high quality signals that are not duplicative of signals from neighboring rings. By way of a non-limiting example only, each ring may have a width 1112 of between 2-5 mm, or more or less, and the rings may have a spacing 1114 of at least 2-5 mm apart. In some exemplary, non-limiting implementations, the rings and/or other conductive element(s) may have thinner widths (e.g., no more than 1-2 mm) and/or spacings (e.g., no more than 1-2 mm apart) to ensure that a sufficient number of rings make contact with different parts of the ear canal and/or provide a minimum signal to noise ratio (e.g., 10 dB, 20 dB or more or less). In some implementations, if certain elements do not provide signals of selected quality, the data received from those elements may be discarded by the on-board and/or remote processing system.

In some exemplary implementations, any and/or all of the contacts may have non-ring shapes, so long as the contacts circumscribe the outer surface of the housing and/or otherwise provide sufficient signal coverage. These and/or other electrode shapes may be distributed longitudinally and/or radially along the exterior of the housing.

In some implementations, the result for any of the above configurations may include an orientation agnostic in-ear sensor assembly that does not require the wearer to insert the device in any particular orientation in the ear canal. Further, the device may include one or more physical reference features so that the wearer may more easily place it at the same clocking orientation each time it is worn, which can aid repeatability for sensing signals.

Figure 12:
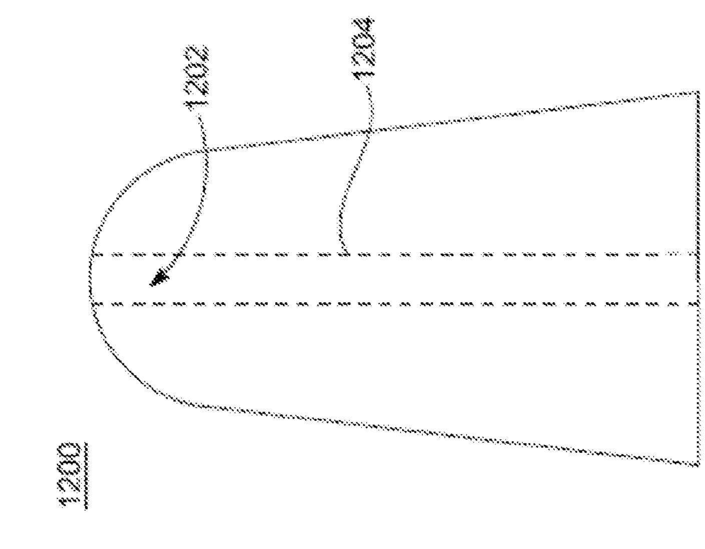
FIG. 12 illustrates a cutaway view of a sensor unit, according to some implementations of the current subject matter.

It may be desirable to allow the wearer to hear ambient sounds while the sensor unit is worn. This will avoid the sensation of the device being an ear plug, and will be more conducive to wearing for an extended period of time (e.g., hours or days). To achieve this, the sensor unit may include one or more holes and/or tubes extending generally along the longitudinal axis for sound to pass through. FIG. 12 illustrates a cutaway view 1200 of one such example. As shown in FIG. 12, a generally cylindrical hole 1202 defined by sidewall(s) 1204 may extend substantially and/or completely through the housing.

In some implementations, one or more hole(s) may be formed as part of the malleable housing, and may remain open after insertion into the ear canal. Alternatively, or in addition to, one or more tubes of a non-collapsible (rigid or semi-rigid) material may be inserted into and/or fabricated as part of the housing. The tubes may prevent pinching and/or crimping of the foam and/or other malleable housing material, thereby allowing the wearer to hear ambient sounds without appreciable distortion (e.g., without cutting off and/or attenuating higher frequencies beyond 10-15 kHz) and/or reduction in volume. In some implementations, in place of and/or in addition to the hole(s), a small speaker may be incorporated into the malleable housing. The speaker may provide sound to the inner portions of the ear canal. The speaker may emit sounds in place of and/or to augment sounds passed through the hole(s).

Example Operation

Upon insertion into the ear canal, the sensor assembly may be configured to detect signals, such as EEG (electroencephalography) waves (which can include alpha, beta, gamma, delta, etc.) or other waves. Processing of such signals may be performed at the sensor assembly, by a remote processing system, or both. FIG. 13A illustrates one example of an on-board processing system 1300, and FIG. 13B illustrates one example of a remote processing system 1350, according to some implementations of the current subject matter. With regard to FIG. 13A, the signals from the electrodes (e.g., rings 302 and/or dots 402) may first be received by an analog front end (AFE) 1302. The AFE 1302 may provide one or more of signal buffering via buffer 1304, filtering via filter(s) 1306, signal amplification by amplifier 1308, and/or analog to digital conversion by the analog to digital converter (ADC) 950. As noted in FIG. 13A, the (ADC) 950 may be integrated with the processing system 1300 "on-board" the in-ear device to provide a complete in-ear system that does not need a separate, remote module for processing.

The processing system 1300 may also receive biometric and other information from additional sensors, such as a temperature sensor 1312, a heart rate sensor 1314 and an accelerometer 1316. While not illustrated in FIG. 13A, as noted above other sensors may include EDA sensors such as galvanic skin response sensors, a pulse oximeter sensor, a glucometer, as well as orientation sensors and/or location sensors. Some or all of this information may also be processed by AFE 1302. The processing system 1300 at FIG. 13A may also include an interface (e.g., a wired or wireless connection) to a physiological sensor.

The processing system 1300 may analyze the obtained data with an on-board processor module 1318, which may include one or more processors 1320 as well as memory 1322 that may store instructions 1324 and data 1326 that may be executed or otherwise used by the processor(s) 1320. The one or more processors 1320 may be, e.g., a controller or CPU. Alternatively, the one or more processors 1320 may be a dedicated device such as an ASIC, FPGA or other hardware-based device. The memory 1322 may be of any type capable of storing information accessible by the processor(s) in a non-transitory manner, such as solid state flash memory or the like.

The instructions 1324 may be any set of instructions to be executed directly (such as machine code) or indirectly (such as scripts) by the processor(s). For example, the instructions may be stored as computing device code in the non-transitory memory. In that regard, the terms "instructions" and "programs" may be used interchangeably herein. The instructions may be stored in object code format for direct processing by the processor(s), or in any other computing device language including scripts or collections of independent source code modules that are interpreted on demand or compiled in advance. The data 1326 may be retrieved, stored or modified by one or more processors in accordance with the instructions 1324. As an example, data 1326 may include heuristics to be used when calibrating or evaluating electrode viability, for instance to rank electrode suitability based on signal-to-noise ratio or other metrics.

As noted above, in one example a speaker 1327 may be incorporated into the malleable housing. The speaker 1327 is operatively coupled to the on-board processor module 1318 to provide sound to the inner portions of the canal. The module 1318 may actuate the speaker 1327 to supplement (augment) sounds passed through the hole(s) extending through the malleable housing, or to generate different sounds such as audible cues (e.g., tones) to provide information or give aural feedback to the wearer.

Alternatively or in addition to on-board signal analysis, the processing system may transmit the obtained data to remote processing system 1350. This may be done, for instance, via a wireless transceiver 1328 or a wired link 1330, such as I2C, SPI, Universal Asynchronous Receiver/Transmitter (UART), I2S, or some other low-signal count communications path. In the latter case, the FPC may extend out the end of the sensor assembly and be physically coupled to remote processing system 1350 that can receive and/or process the obtained bio signals. Alternatively, in the former case the wireless transceiver the FPC may communicate with the remote processing system 1350 via Bluetooth™, Bluetooth™ LE, near field communication (NFC) or some other wireless communication method.

System 1300 may include a battery 1332 to power the components of the processing system. It may also include a battery charger 1334. The battery charger may be contactless, and/or may be plugged into an external power source to charge the battery. The system 1300 may be incorporated into and/or mounted on the FPC. Alternatively, or in addition to, some or all of the system 1300 may be received within the housing and operatively coupled to the FPC as needed for receiving sensor data and/or transmitting information to the remote processing system 1350.

FIG. 13B illustrates an exemplary remote processing system 1350 that may include a transceiver 1352, according to some implementations of the current subject matter. The transceiver 1352 may be configured to communicate with one or both of wireless transceiver 1328 and wired link 1330. The system 1350 may include a power supply 1354, which may include batteries and/or a connection for an outlet or the like. The information received from the on-board processing system 1300, whether raw or unprocessed, may be passed from the transceiver 1352 to the off-board processor module 1356.

The off-board processor module 1356 may be configured to analyze the obtained data with one or more processors 1358 as well as memory 1360 that stores instructions 1362 and data 1364 that may be executed or otherwise used by the processor(s) 1358, in a manner similar to described above. The one or more processors 1320 may be, e.g., a controller or CPU. Alternatively, or in addition to, the one or more processors 1320 may be a dedicated device such as a DSP, an ASIC, FPGA or other hardware-based device. The memory 1322 may be of any type capable of storing information accessible by the processor(s) in a non-transitory manner, such as solid state flash memory, hard disc, optical medium or the like.

The off-board processor module 1356 may include a user interface subsystem 1366, which may be used to present information regarding the processed data to the earpiece wearer, a technician, doctor or other authorized user.

Most existing integrated neural interfaces can measure electrical potentials, while few provide current stimulation, or current-clamping, through the same recording electrodes. However, existing systems do not include integrated solutions providing voltage-clamping and current recording for characterizing ion currents through membranes and voltammetry of neurotransmitter redox activity. The current subject matter system (e.g., the systems discussed herein with regard to FIGS. 1-13B) that includes NiSoC serial programmable interface may be used to configure one or more recordings by setting gain, bandwidth, and/or current- or voltage-clamping modes. Analog-to-digital conversion may be handled using a power-saving, LSB-first dynamic incremental SAR (iSAR) with wide range for neural signals (e.g., action potentials, local field potentials, and/or surface electrophysiology). The on-chip ADCs may be controlled using logic, which may require a counter reset, counter increment, and/or a store index on-chip signal.

Figure 14:
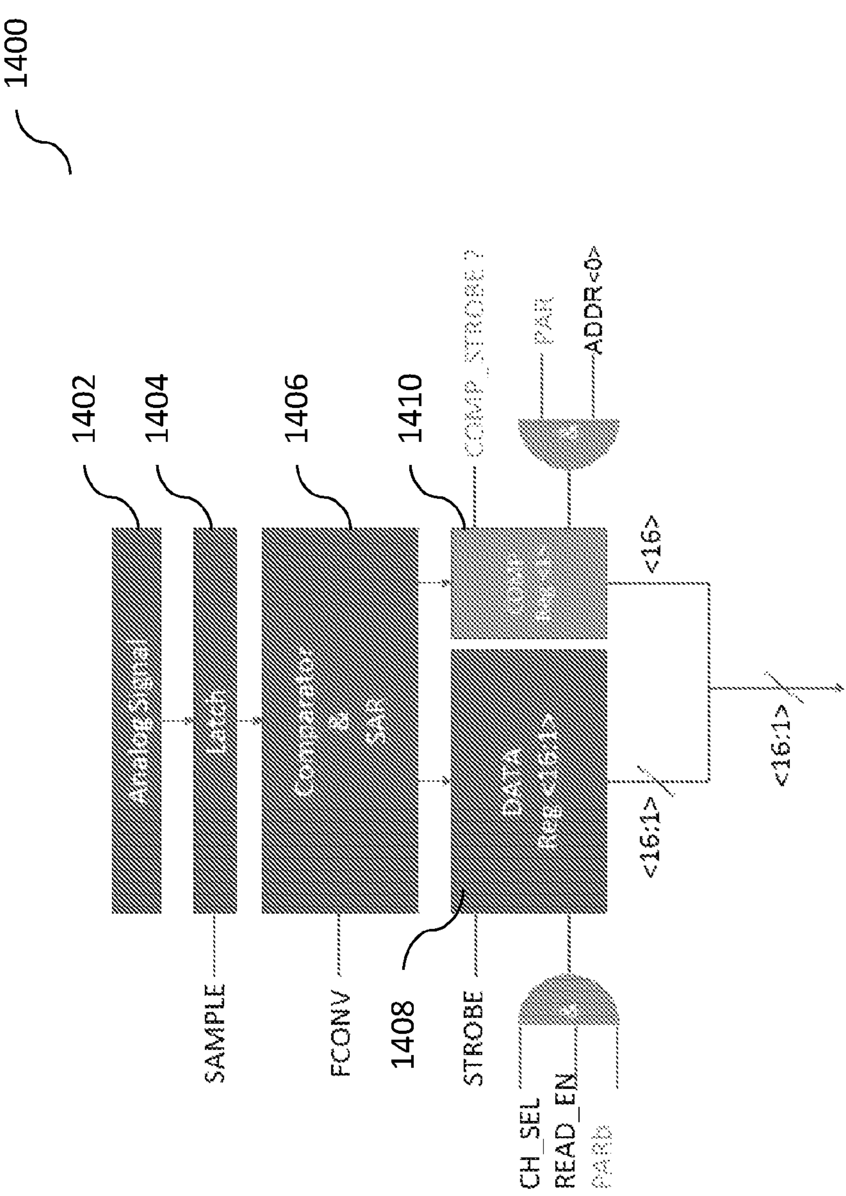
FIG. 14 illustrates an exemplary single input channel, according to some implementations of the current subject matter.

FIG. 14 illustrates an exemplary single input channel 1400, according to some implementations of the NISOC with analog front-end 1402 directly coupled to a dynamic incremental ADC with sample-and-hold 1404, comparator, and SAR 1406, and with time-multiplexed parallel 1408 or bit-serial 1410 digital readout. Analog inputs to AFE 1400 can come from physiological interface devices such as 900 where sensors 912 conduct signals along wires or traces 910 and 906 with or without pre-amplification 908 to interface AFE connector 914. Analog clamping signals generated in 1402 per configuration of current clamp switch 222 and voltage clamp switch 232 from current source 204 and voltage source 206, respectively, can be output into physiological sensor 912, 1102 along analog paths 906, 910 for, but not limited to, stimulation, impedance scanning, and lead-off detection.

Figure 15:
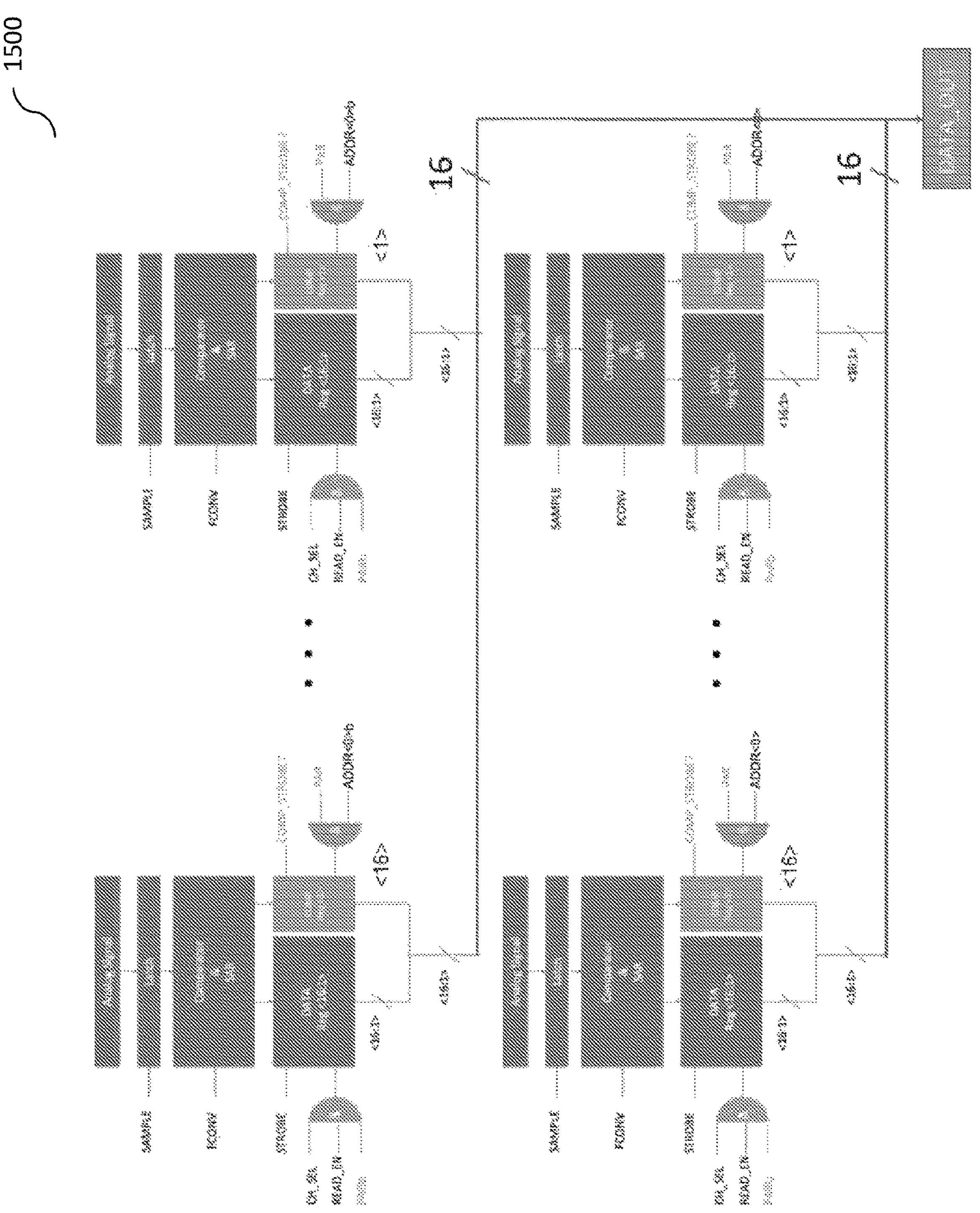
FIG. 15 illustrates an exemplary multichannel read-in and write-out channel, according to some implementations of the current subject matter.

FIG. 15 illustrates an exemplary multichannel read-in and write-out channel 1500, combining the time-multiplexed digital readout from multiple simultaneously sampling input channels 1400. Multichannel read-in for settings, configuration, and initial start conditions, amongst other things, between the on-board processor 1318 and channel read-in/write-out 1500 can be performed on a local channel specific level or a global, channel-wide level per the read-in control 1410.

Figure 16:
FIG. 16 illustrates an exemplary serial peripheral interface (SPI), according to some implementations of the current subject matter.
Figure 16:
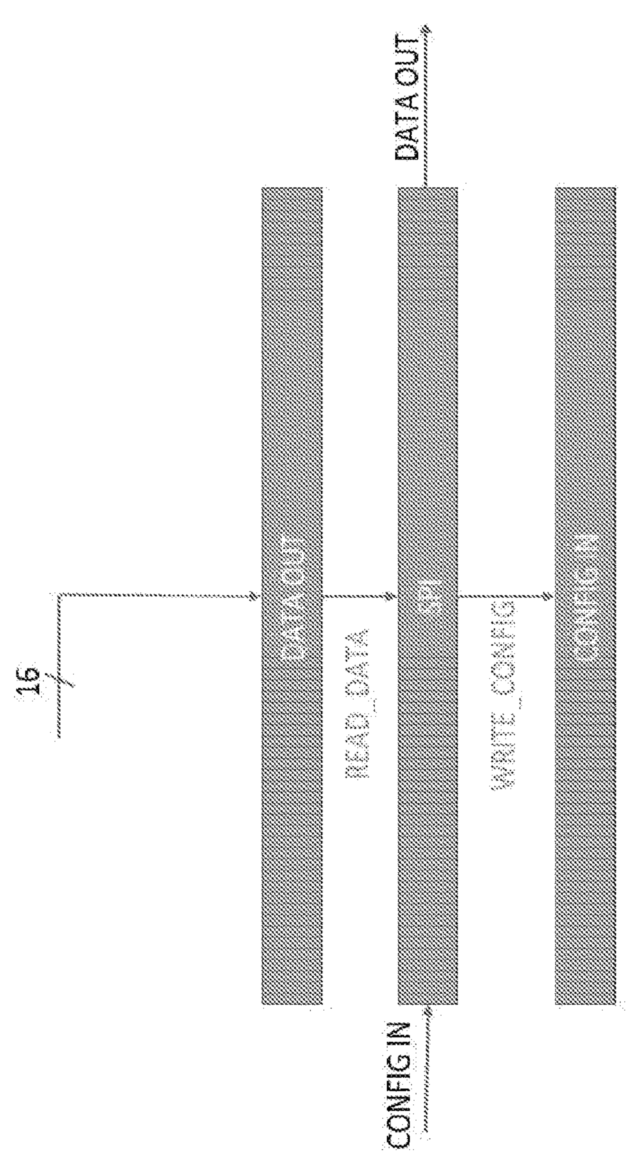

FIG. 16 illustrates an exemplary serial peripheral interface (SPI) 1600, optionally providing bit-serial output of time-multiplexed digital readout 1500.

Figures 17A, 17B, 17C:
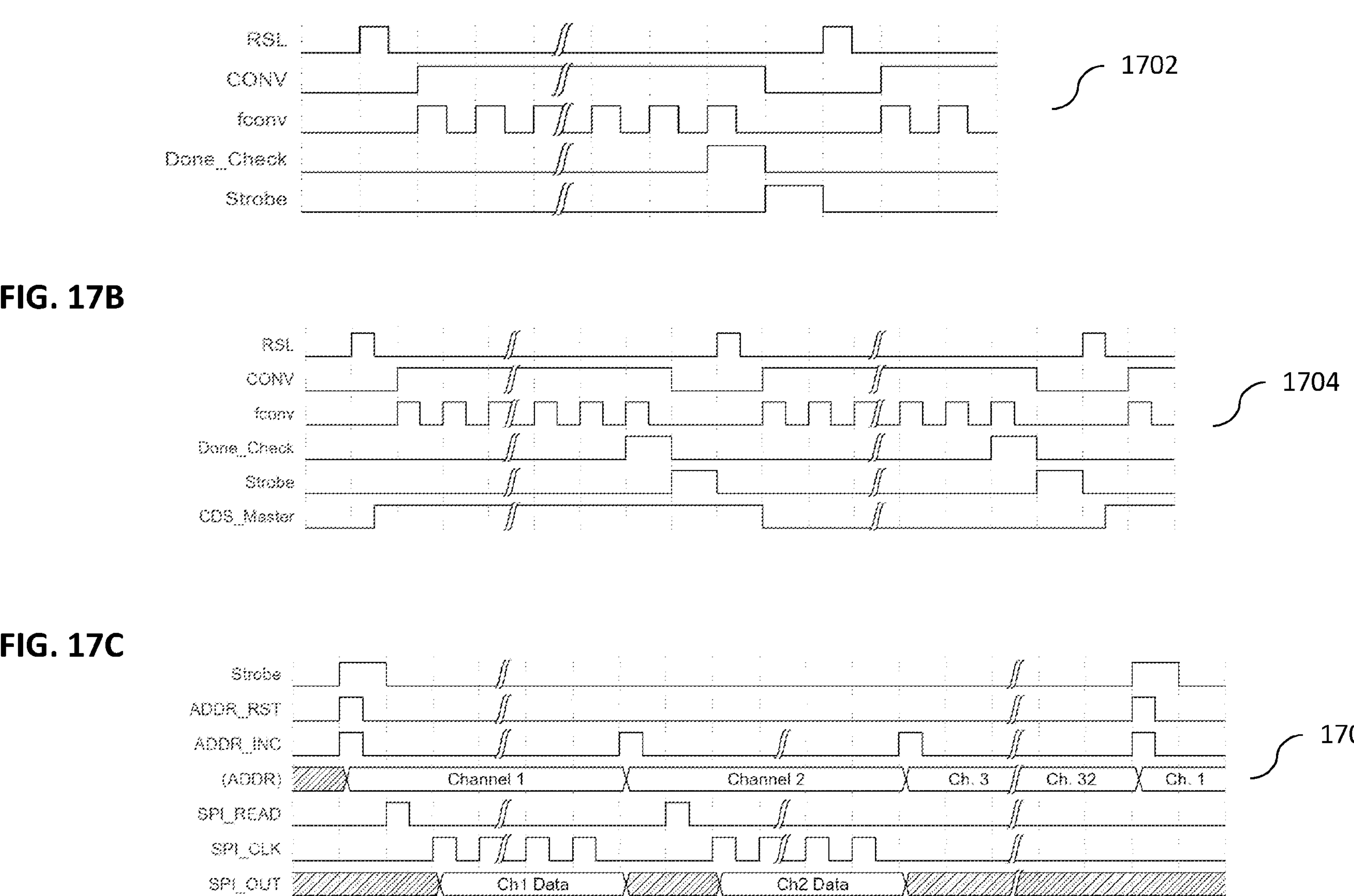
FIGS. 17A-C illustrate various timing diagrams that may be generated by the systems shown in FIGS. 14-16, according to some implementations of the current subject matter.

FIGS. 17A-C illustrate various timing diagrams 1702-1706 that may be generated to configure and control the operation of the NISOC with reference to its components shown in FIGS. 14-16. The timing diagram 1702 illustrates single basic sampling plots. In particular, diagram 1702 illustrates five signals (assuming configuration registers have already been loaded): reset-sample-load (RSL) that initiates analog sample conversion to digital indicated by a short positive step from VSS to DVDD, then back to VSS for the duration of the conversion period, as indicated by the CONV high signal. By way of a non-limiting example, in a 32-channel implementation of one or more systems discussed above with regard to FIGS. 14-16, fconv signal may be a 2 MHz clock signal with less than 50% duty cycle. Upon completion of the conversion, a done signal (Done_Check signal) may be generated which may share its falling edge with the CONV signal. The Strobe signal may shift data out of the ADC into a buffer register to be read out into the SPI.

Timing diagram 1704 may be representative of the voltage correlated double sampling (CDS). It includes the signals shown in the timing diagram 1702 (i.e., RSL, CONV, fconv, Done_Check) in addition to the Strobe and CDS_Master signals. For operating in voltage correlated double sampling mode, a CDS_Master signal may be supplied at a period twice that of a single ADC conversion period. While High, correlated double sampling may be enabled, and while Low, it may be disabled. The double integral symbols in the signal diagrams may indicate a region of the timing diagram which may be repetitive and thus, reduced for condensing the diagram. In all usage of the double integral, the same amount of time may be shown as condensed.

Timing diagram 1706 may be representative of a SPI read. The illustrated signals include Strobe, ADDR_RST, ADDR_INC, (ADDR), SPI READ, SPI_CLK, and SPI_OUT. The SPI bus of one or more systems shown in FIG. 16, which may include SPI_IN, SPI_CLK, SPI_OUT, and SPI logic control signals that may run through the center of one or more systems shown in FIG. 14 for basic single chip SPI, and/or multi-slave daisy-chain SPI. The SPI pads may be separated with AVDD and DVDD pads to isolate the digital readout signals from sensitive reference and bias voltage input and analog test output pads.

In view of the above-described implementations of subject matter this application discloses the following list of examples, wherein one feature of an example in isolation or more than one feature of said example taken in combination and, optionally, in combination with one or more features of one or more further examples are further examples also falling within the disclosure of this application:

Example 1: A system, comprising: an in-ear housing configured to fit in an ear of a wearer; a flexible printed circuit mounted within the in-ear housing; and an analog to digital converter comprising a neural interface system-on-chip having dynamic incremental successive-approximation register acquisition to process signals detected by at least one electrode disposed on or near a surface of the in-ear housing.

Example 2: The system of Example 1, wherein the in-ear housing comprises a malleable material that compresses for insertion into an ear canal of the wearer to enable contact at one or more points within the ear canal.

Example 3: The system of any of Examples 1-2, wherein the flexible printed circuit board includes one or more conductive wires, wherein the conductive wires each terminate at a corresponding electrode that senses signals and carry the signals to a common interface, wherein the common interface is coupled to the analog to digital converter.

Example 4: The system of any of Examples 1-3, wherein the analog to digital converter is remote from the in-ear housing.

Example 5: The system of any of Examples 1-4, wherein the analog to digital converter is contained within the in-ear housing.

Example 6: The system of any of Examples 1-5, wherein the at least one electrode comprises a plurality of electrodes arranged as a plurality of conductive rings positioned on the exterior surface of the in-ear housing.

Example 7: The system of any of Examples 1-6, wherein the analog to digital converter is comprised in a processing system including an analog front end, wherein the analog front end couples to a buffer, a filter, and a signal amplifier to process and convert the signals.

Example 8: The system of any of Examples 1-7, wherein the processing system further includes one or more of the following: a temperature sensor to sense temperature of a wearer of the in-ear housing, a heart rate sensor to sense a heart rate of the wearer, an accelerometer, a wireless transceiver, a wired link, a speaker, at least one processor, at least one memory, a source of power.

Example 9: The system of any of Examples 1-8, wherein the processing system couples via a wireless link to a remote processing system, wherein the remote processing system includes one or more of the following: a wireless transceiver to communicate with a corresponding wireless transceiver at the processing system, at least one processor, at least one memory, a source of power, a user interface subsystem from which information regarding data processed by the processing system and/or remote processing system may be obtained for further processing or viewing.

Example 10: The system of any of Examples 1-10, wherein the signals comprise one or more of the following: an electroencephalography (EEG) of a wearer, an electrooculography (EOG) of a wearer, a temperature of the wearer, a heart rate of the wearer, sound, and acceleration.

Example 11: A method comprising: detecting, by at least one electrode, signals, wherein the at least one electrode is disposed in on or near a surface of an in-ear housing, wherein the in-ear housing configured to fit in an ear of a wearer, wherein the in-ear housing is comprised in a system further including a flexible printed circuit mounted within the in-ear housing and an analog to digital converter comprising a neural interface system-on-chip having dynamic incremental successive-approximation register acquisition; and converting, by the analog to digital converter comprising the neural interface system-on-chip signals, the detected signals to a digital form.

Example 12: The method of Example 11, wherein the in-ear housing comprises a malleable material that compresses for insertion into an ear canal of the wearer to enable contact at one or more points within the ear canal.

Example 13: The method of any of Examples 11-12, wherein the flexible printed circuit board includes one or more conductive wires, wherein the conductive wires each terminate at a corresponding electrode that senses signals and carry the signals to a common interface, wherein the common interface is coupled to the analog to digital converter.

Example 14: The method of any of Examples 11-13, wherein the analog to digital converter is remote from the in-ear housing.

Example 15: The method of any of Examples 11-13, wherein the analog to digital converter is contained within the in-ear housing.

Example 16: The method of any of Examples 11-15, wherein the at least one electrode comprises a plurality of electrodes arranged as a plurality of conductive rings positioned on the exterior surface of the in-ear housing.

Example 17: The method of any of Examples 11-16, wherein the analog to digital converter is comprised in a processing system including an analog front end, wherein the analog front end couples to a buffer, a filter, and a signal amplifier to process and convert the signals.

Example 18: The method of any of Examples 11-17, wherein the processing system further includes one or more of the following: a temperature sensor to sense temperature of a wearer of the in-ear housing, a heart rate sensor to sense a heart rate of the wearer, an accelerometer, a wireless transceiver, a wired link, a speaker, at least one processor, at least one memory, a source of power.

Example 19: The method of any of Examples 11-18, wherein the processing system couples via a wireless link to a remote processing system, wherein the remote processing system includes one or more of the following: a wireless transceiver to communicate with a corresponding wireless transceiver at the processing system, at least one processor, at least one memory, a source of power, a user interface subsystem from which information regarding data processed by the processing system and/or remote processing system may be obtained for further processing or viewing.

Example 20: The method of any of Examples 11-19, wherein the signals comprise one or more of the following: an electroencephalography (EEG) of a wearer, an electrooculography (EOG) of a wearer, a temperature of the wearer, a heart rate of the wearer, sound, and acceleration.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. For example, the logic flows may include different and/or additional operations than shown without departing from the scope of the present disclosure. One or more operations of the logic flows may be repeated and/or omitted without departing from the scope of the present disclosure. Other implementations may be within the scope of the following claims.

What is claimed:

1. A system, comprising:

an in-ear housing configured to fit in an ear of a wearer;

a flexible printed circuit mounted within the in-ear housing; and an analog to digital converter comprising a neural interface system-on-chip having dynamic incremental successive-approximation register and a counter to process signals detected by at least one electrode disposed on or near a surface of the in-ear housing, wherein the dynamic incremental successive-approximation register comprising the counter is set, in a first cycle, to a first index value, wherein the first index value is a previous output result of the analog to digital converter.

2. The system of claim 1, wherein in at least a second cycle, the counter is configured with a second index value, wherein until a voltage of the analog to digital converter crosses a threshold defined by an amplifier voltage, the second index value increases from the first index value by 1 and in response to the cross of the threshold, the second index value decreases by a value of 1, and wherein the in-ear housing comprises a malleable material that compresses for insertion into an ear canal of the wearer to enable contact at one or more points within the ear canal.

3. The system of claim 1, wherein the flexible printed circuit board includes one or more conductive wires, wherein the conductive wires each terminate at a corresponding electrode that senses signals and carry the signals to a common interface, wherein the common interface is coupled to the analog to digital converter.

4. The system of claim 1, wherein the analog to digital converter is remote from the in-ear housing.

5. The system of claim 1, wherein the analog to digital converter is contained within the in-ear housing.

6. A system comprising:

an in-ear housing configured to fit in an ear of a wearer;

a flexible printed circuit mounted within the in-ear housing; and an analog to digital converter comprising a neural interface system-on-chip having dynamic incremental successive-approximation register and a counter to process signals detected by at least one electrode disposed on or near a surface of the in-ear housing, wherein the at least one electrode comprises a plurality of electrodes arranged as a plurality of conductive rings positioned on the exterior surface of the in-ear housing, wherein the plurality of conductive rings are spaced, between a first end of the in-ear housing and a second end of the in-ear housing along a longitudinal axis of the in-ear housing;

wherein the dynamic incremental successive-approximation register comprising the counter is set, in a first cycle, to a first index value, wherein the first index value is a previous output result of the analog to digital converter; and wherein in at least a second cycle, the counter is configured with a second index value, wherein until a voltage of the analog to digital converter crosses a threshold defined by an amplifier voltage, the second index value increases from the first index value by 1 and in response to the cross of the threshold, the second index value decreases by a value of 1.

7. The system of claim 1, wherein the analog to digital converter is comprised in a processing system including an analog front end, wherein the analog front end couples to a buffer, a filter, and a signal amplifier to process and convert the signals.

8. The system of claim 7, wherein the processing system further includes one or more of the following: a temperature sensor to sense temperature of a wearer of the in-ear housing, a heart rate sensor to sense a heart rate of the wearer, an accelerometer, a wireless transceiver, a wired link, a speaker, at least one processor, at least one memory, a source of power.

9. The system of claim 7, wherein the processing system couples via a wireless link to a remote processing system, wherein the remote processing system includes one or more of the following: a wireless transceiver to communicate with a corresponding wireless transceiver at the processing system, at least one processor, at least one memory, a source of power, a user interface subsystem from which information regarding data processed by the processing system and/or remote processing system may be obtained for further processing or viewing.

10. The system of claim 1, wherein the signals comprise one or more of the following: an electroencephalography (EEG) of a wearer, an electrooculography (EOG) of a wearer, a temperature of the wearer, a heart rate of the wearer, sound, and acceleration.

11. A method comprising:

detecting, by at least one electrode, signals, wherein the at least one electrode is disposed in on or near a surface of an in-ear housing, wherein the in-ear housing configured to fit in an ear of a wearer, wherein the in-ear housing is comprised in a system further including a flexible printed circuit mounted within the in-ear housing and an analog to digital converter comprising a neural interface system-on-chip having dynamic incremental successive-approximation register and a counter, wherein the dynamic incremental successive-approximation register comprising the counter is set, in a first cycle, to a first index value, wherein the first index value is a previous output result of the analog to digital converter; and converting, by the analog to digital converter comprising the neural interface system-on-chip signals, the detected signals to a digital form.

12. The method of claim 11, wherein the in-ear housing comprises a malleable material that compresses for insertion into an ear canal of the wearer to enable contact at one or more points within the ear canal.

13. The method of claim 11, wherein the flexible printed circuit board includes one or more conductive wires, wherein the conductive wires each terminate at a corresponding electrode that senses signals and carry the signals to a common interface, wherein the common interface is coupled to the analog to digital converter.

14. The method of claim 11, wherein the analog to digital converter is remote from the in-ear housing.

15. The method of claim 11, wherein the analog to digital converter is contained within the in-ear housing.

16. The method of claim 11, wherein the at least one electrode comprises a plurality of electrodes arranged as a plurality of conductive rings positioned on the exterior surface of the in-ear housing.

17. The method of claim 11, wherein the analog to digital converter is comprised in a processing system including an analog front end, wherein the analog front end couples to a buffer, a filter, and a signal amplifier to process and convert the signals.

18. The method of claim 17, wherein the processing system further includes one or more of the following: a temperature sensor to sense temperature of a wearer of the in-ear housing, a heart rate sensor to sense a heart rate of the wearer, an accelerometer, a wireless transceiver, a wired link, a speaker, at least one processor, at least one memory, a source of power.

19. The method of claim 17, wherein the processing system couples via a wireless link to a remote processing system, wherein the remote processing system includes one or more of the following: a wireless transceiver to communicate with a corresponding wireless transceiver at the processing system, at least one processor, at least one memory, a source of power, a user interface subsystem from which information regarding data processed by the processing system and/or remote processing system may be obtained for further processing or viewing.

20. The method of claim 11, wherein the signals comprise one or more of the following: an electroencephalography (EEG) of a wearer, an electrooculography (EOG) of a wearer, a temperature of the wearer, a heart rate of the wearer, sound, and acceleration.

* * * * *